(12) United States Patent
Wood et al.

(10) Patent No.: US 7,537,912 B2
(45) Date of Patent: May 26, 2009

(54) METHODS OF MEASURING LUMINOGENIC ACTIVITY WITH A PROTECTED COELENTERAZINE

(75) Inventors: Keith Wood, Mt. Horeb, WI (US); Erika Hawkins, Madison, WI (US); Mike Scurria, San Luis Obispo, CA (US); Dieter Klaubert, Arroyo Grande, CA (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 11/832,169

(22) Filed: Aug. 1, 2007

(65) Prior Publication Data

US 2008/0050760 A1  Feb. 28, 2008

Related U.S. Application Data

(62) Division of application No. 10/053,482, filed on Nov. 2, 2001, now Pat. No. 7,268,229.

(51) Int. Cl.
*C12Q 1/44* (2006.01)

(52) U.S. Cl. .............................. 435/19; 435/8; 544/242; 544/245

(58) Field of Classification Search ................... 435/19, 435/8; 544/242, 245; 546/268.4
See application file for complete search history.

(56) References Cited

U.S. PATENT DOCUMENTS

| | | | |
|---|---|---|---|
| 3,958,938 A | 5/1976 | Doonan et al. | |
| 4,080,265 A | 3/1978 | Antonik | |
| 4,349,510 A | 9/1982 | Kolehmainen et al. | |
| 4,501,813 A | 2/1985 | Lovgren et al. | |
| 4,604,364 A | 8/1986 | Kosak | |
| 4,665,022 A | 5/1987 | Schaeffer et al. | |
| 4,806,415 A | 2/1989 | Fossati | |
| 5,023,181 A | 6/1991 | Inouye | |
| 5,035,999 A | 7/1991 | Geiger et al. | |
| 5,098,828 A | 3/1992 | Geiger et al. | |
| 5,246,834 A | 9/1993 | Tsuji et al. | |
| 5,374,534 A | 12/1994 | Zomer et al. | |
| 5,374,535 A | 12/1994 | Zomer et al. | |
| 5,518,883 A | 5/1996 | Soini | |
| 5,541,309 A | 7/1996 | Prasher | |
| 5,587,286 A | 12/1996 | Pahuski et al. | |
| 5,641,641 A | 6/1997 | Wood | |
| 5,648,232 A | 7/1997 | Squirrell | |
| 5,650,289 A | 7/1997 | Wood | |
| 5,650,299 A | 7/1997 | Lawman et al. | |
| 5,700,645 A | 12/1997 | Pahuski et al. | |
| 5,741,668 A | 4/1998 | Ward et al. | |
| 5,770,391 A | 6/1998 | Foote et al. | |
| 5,798,263 A | 8/1998 | Wood et al. | |
| 5,811,251 A | 9/1998 | Hirose et al. | |
| 5,814,471 A | 9/1998 | Wood | |
| 5,831,102 A | 11/1998 | Bronstein et al. | |
| 5,840,572 A | 11/1998 | Copeland et al. | |
| 5,891,659 A | 4/1999 | Murakami et al. | |
| 5,891,702 A | 4/1999 | Sakakibara et al. | |
| 5,908,751 A | 6/1999 | Higo et al. | |
| 5,965,453 A | 10/1999 | Skiffington et al. | |
| 6,004,767 A | 12/1999 | Crouch et al. | |
| 6,007,996 A | 12/1999 | McNamara et al. | |
| 6,133,459 A | 10/2000 | Schaap et al. | |
| 6,165,734 A | 12/2000 | Garini et al. | |
| 6,171,809 B1 | 1/2001 | Roelant | |
| 6,214,552 B1 * | 4/2001 | Heroux et al. | .................. 435/6 |
| 6,416,960 B1 | 7/2002 | Bryan | |
| 6,436,682 B1 | 8/2002 | Bryan et al. | |

FOREIGN PATENT DOCUMENTS

| | | | |
|---|---|---|---|
| EP | WO 01/87853 A1 | | 11/2001 |
| JP | 8-59686 | * | 3/1996 |
| JP | 8-294397 | | 3/1996 |
| JP | 8059686 | | 3/1996 |
| JP | 8-59686 | | 11/1996 |
| JP | 8-294397 | * | 11/1996 |
| WO | WO 99/66324 | | 12/1999 |

OTHER PUBLICATIONS

Theodora W. Greene and Peter G. M. Wuts. "Monoprotection of Dicarbonyl Compunds", in Protective Groups in Organic Synthesis—2nd edition (John Wiley 1991).

Shoji Inoue et al., "Complete Structure of *Renilla* Luciferin and Luciferyl Sulfate", Tetrahedron Letters No. 31, pp. 2685-2688 (1977).

R. Y. Tsien, "A non-disruptive technique for loading calcium buffers and indicators into cells", Nature, vol. 290, pp. 527-528 (Apr. 9, 1981).

Peter R. Redden et al., "Acyloxymethyl acidic drug derivatives: in vitro hydrolytic reactivity", International Journal of Pharmaceutics, vol. 180, pp. 151-160 (1999).

Katsunori Teranishi and Osamu Shimomura, "Coelenterazine Analogs as Chemiluminescent Probe for Superoxide Anion", Analytical Biochemistry 249: pp. 37-43 (1997).

Osamu Shimomura et al., "Semi-synthetic aequorins with improved sensitivity to $Ca^{2+}$ ions", Biochem. J. 261: pp. 913-920 (1989).

Satoshi Inouye and Osamu Shimomura, "The use of *Renilla* Luciferase, *Oplophorus* Luciferase, and Apoaequorin as Bioluminescent Reporter Protein in the Presence of Coelenterazine Analogues as Substrate", Biochemical and Biophysical Research Communications 233: 349-353 (1997).

Keith Jones et al., "Glowing jellyfish, luminescence and a molecule called coelenterazine", Tibtech vol. 17, pp. 477-481 (1999).

Osamu Shimomura and Katsunori Teranishi, "Light-emitters involved in the luminescence of coelenterazine", Luminescence 15: 51-58 (2000).

(Continued)

*Primary Examiner*—Ralph Gitomer
(74) *Attorney, Agent, or Firm*—Brinks Hofer Gilson & Lione

(57) ABSTRACT

A method of measuring the enzymatic activity of a luciferase includes contacting a luminogenic protein, such as a luciferase, with a protected luminophore to form a composition; and detecting light produced from the composition. The protected luminophore provides increased stability and improved signal-to-background ratios relative to the corresponding unmodified coelenterazine.

25 Claims, 3 Drawing Sheets

OTHER PUBLICATIONS

Osamu Shimomura et al., "The relative rate of aequorin regulation from apoaequorin and coelenterazine analogues", Biochem. J. 296: 549-551 (1993).

Osamu Shimomura, "Membrane permeability of coelenterazine analogues measured with fish eggs", Biochem. J. 326: 297-298 (1997).

"Coelenterazine and Coelenterazine Derivatives", Molecular Probes—Product information pp. 1-3 (Apr. 4, 2000).

"Coelenterazine Sampler Kit", Molecular Probes—Product Literature, pp. 1-3 (Oct. 16, 2000).

Dubuisson, M. L. et al., "Antioxidative properties of natural coelenterazine and synthetic methyl coelenterazine in rat hepatocytes subjected to tert-butyl hydroperoxide-induced oxidative stress", Biochem-Pharmacol. 60(4): pp. 471-478 (2000).

Angers, S. et al., "Detection of beta 2-adrenergic receptor dimerization in living cells using bioluminescence resonance energy transfer (BRET)", Prod. Natl. Accad. Sci. USA 97(7): pp. 3684-3689 (2000).

Liu, J. and Escher, A., "Improved assay sensitivity of an engineered secreted *Renilla* luciferase", Gene 237(1): pp. 153-159 (1999).

Srikantha, T. et al., "The sea pansy *Renilla* reniformis luciferase serves as a sensitive bioluminescent reporter for differential gene expression in *Candida albicans*", J. Bacteriol. 178(1): pp. 121-129 (1996).

Skarpidi, E. et al., "Novel in vitro assay for the detection of pharmacologic inducers of fetal hemoglobin", Blood 96(1): pp. 321-326 (2000).

Parsons, S.J. et al., "Use of a dual firefly and *Renilla* luciferase reporter gene assay to simultaneously determine drug selectivity at human corticotrophin releasing hormone 1 and 2 receptors", Anal. Biochem. 281(2): pp. 187-192 (2000).

Stables, J. et al., "Development of a dual glow-signal firefly and *Renilla* luciferase assay reagent for the analysis of G-protein coupled receptor signalling", J. Recept. Signal Transduct. Res. 19(1-4): pp. 395-410 (1999)—Abstract Only.

Grentzmann, G. et al., "A dual-luciferase reporter system for studying recording signals", RNA 4(4): pp. 479-486 (1998).

Liu, J. et al., "Visualizing and quantifying protein secretion using a *Renilla* luciferase-GFP fusion protein", Luminescence 15(1): pp. 45-49 (2000).

Craig, Frank F. et al., "Membrane-permeable luciferin esters for assay of firefly luciferase in live intact cells" Biochem. J. 276 pp. 637-641 (1991).

Shimomura, O. "Cause of spectral variation in the luminescence of semisynthetic aequorins" *Biochem J.* (1995) 306, 537-543.

Nakamura, H. et al. "Design, Synthesis, and Evaluation of the Transition-State Inhibitors of Coelenterazine Bioluminescence: Probing the Chiral Environment of Active Site" *J. Am. Chem. Soc.* 2001, 123, 1523-1524.

International Search Report for corresponding Patent Cooperation Treaty application No. PCT/US02/34972, dated Feb. 11, 2003, 5 pages.

Mitani, M. et al. Analytical Sciences (1995) 11(6), 1013-1015.

Mitani, M. et al. Analytical Sciences (1994) 10(5), 813-814.

Sakaki, H. et al. Chem. Abstract No. 1997:48722.

Mitani, M. et al. Chem. Abstract No. 1996:335963.

Inoue, S. Chemistry Letters (1987) (2) 417-418.

Inoue, S. Tetrahedron Letters (1977) (31), 2685-8.

Hawkins, E. Bioluminescence & Chemiluminescence: Progress & Current Applications, "Proceeding of the Symposium on Bioiluminescence and Chemiluminescence," 12th, Cambridge, United Kingdom, Apr. 5-9, 2002, 149-152. Editor(s) Stanley, Philip, E.; Kricka, Larry, J., 2002, XP008056546.

Supplementary partial European Search Report (Jan. 16, 2006).

* cited by examiner

METHODS OF MEASURING LUMINOGENIC ACTIVITY WITH A PROTECTED COELENTERAZINE

RELATED APPLICATIONS

This application is a divisional of U.S. patent application Ser. No. 10/053,482, filed on Nov. 2, 2001 now U.S. Pat. No. 7,268,229, which is hereby incorporated by reference in its entirety.

BACKGROUND

Reporter molecules are routinely used to monitor molecular events in the fields of biology, biochemistry, immunology, cell biology and molecular biology. For example, reporter molecules are employed in assays where the levels of the reporter molecule are due to transcription from a specific promoter linked to the reporter molecule. Reporter molecule assays can be used to study biological processes including gene expression, receptor activity, transcription factors, intracellular signaling, mRNA processing, and protein folding. Analysis of reporter molecules that are typically used in such assays includes detection of radioactive isotopes, enzyme activity, fluorescence, or luminescence. This technology is discussed generally by Akhavan-Tafti et al., in: "Bioluminescence and Chemiluminescence. Fundamentals and Applied Aspects. Proceedings of the 8$^{th}$ International Symposium on Bioluminescence and Chemiluminescence." Cambridge, September 1994. Eds. Campbel, Kricka, Stanley. John Wiley and Sons 1994.

Luminescence in biological assays typically involves the activity of a luminogenic protein. Luminogenic proteins that are useful in assay systems include, but are not limited to, *Renilla* luciferase, *Oplophorus* luciferase, *Vargula* (*Cypridina*) luciferase, *Gaussia* luciferase, and aequorin. In a luminescent reaction, the interaction of a luminogenic protein with an appropriate molecule, referred to as a luminophore, produces light as one of the reaction products. The quantity of light (i.e., the number of photons) produced in the reaction, can be measured. This measurement may be used qualitatively to determine if a certain substance is or is not present in a sample. This measurement also may be used quantitatively to calculate the concentration of luminogenic protein and/or luminophore in the reaction.

Luminescent reactions can be used to detect very small quantities of a particular analyte, the substance being identified and measured in an analysis. For example, luminescent reactions can be used to detect and quantify proteases, lipases, phosphatases, peroxidases, glycosidases, various metabolites such as ATP or NADH, and reporter molecules. Luminescent reactions can also be used to detect and quantify analytes through binding interactions, such as those mediated by antibodies and nucleotide probes. Another application of luminescent reactions is bioluminescence resonance energy transfer (BRET), which can determine if two molecules are capable of binding each other or are co-localized in a cell (Angers et al., *Proc. Natl. Acad. Sci. U.S.A.* 97(7):3684-9, 2000). Typically, luminescent reactions can be used to detect an analyte present in a sample at less than about $1\times10^{-16}$ molar, often less than $1\times10^{-19}$ molar.

When using luminescence to measure an analyte, it is preferred that little or no light is produced by reactions that are not dependent on the presence of the analyte. For example, under assay conditions typically used for *Renilla* luciferase, light can generally be detected even when the luminogenic protein is not present. Luminescence that is not dependent on the catalytic activity of a luminogenic protein is termed autoluminescence. This autoluminescence is considered "background" since it does not provide meaningful information about the system but does contribute to the overall luminescent output. Autoluminescence can limit the usefulness of an analytical assay by reducing the ability to measure accurately the quantity of light resulting from the activity of the analyte (ie. "signal"). This can be especially problematic if the magnitude of the noise is significant relative to the magnitude of the actual signal. This measurement uncertainty can be quantified in terms of the ratio of the magnitudes of the signal (S) and the background (B), or signal-to-background ratio (S/B).

Autoluminescence can be caused, for example, by spontaneous oxidation of the luminophore. Also, addition to the assay system of various components, such as lipids (especially above the critical micelle concentration or CMC), hydrophobic proteins (especially those with a defined three-dimensional structure), and cells or other biological materials containing hydrophobic microenvironments, can greatly increase autoluminescence.

One class of luminophores that can exhibit autoluminescence is the coelenterazines. Coelenterazines interact with a variety of marine luciferases to produce light due to the oxidation of the coelenterazine to its respective coelenteramide. If this oxidation is facilitated by a luminogenic protein, then the photon corresponds to the interaction between the substrate and the protein, thus producing a signal. Coelenterazines can also contribute to the background due to spontaneous luminescent oxidation when in solution, even when there is no luminogenic protein present. In addition to producing background, this instability can also cause the luminescent signal to be short lived. This can result in a need to measure the luminescence of many samples in a short period of time, introducing further uncertainty into the overall analysis.

Modifications of coelenterazines have been investigated in attempts to modify their luminescent response. Properties of coelenterazines which have been affected include sensitivity to calcium ions ($Ca^{2+}$) (Shimomura et al., *Biochem. J.* 296: 549-551, 1993; Shimomura et al., *Biochem. J.* 261: 913-920, 1989); sensitivity to superoxide anion ($O_2^-$) (Teranishi et al., *Anal. Biochem.* 249: 37-43, 1997); specificity for individual luminogenic proteins (Inouye et al., *Biochem. Biophys. Res. Comm.* 233: 349-53, 1997); and permeation of cell membranes (Shimomura, *Biochem. J.* 326: 297-298, 1997). Typically, the derivatives differ from natural coelenterazine through the identity of the substituents attached to the core imidazopyrazine structure. Despite their improvements in certain assay environments, these modified coelenterazines are not reported to avoid the problem of autoluminescence.

It is thus desirable to provide compositions which can function, either directly or indirectly, as luminophores and which provide for reduced autoluminescence under normal use conditions. These compositions may further exhibit increased stability relative to conventional luminophores. It is also desirable to provide compositions which are sensitive to substances other than luminogenic proteins. The interaction of such a composition with these substances could convert the composition into a luminophore. Such multi-functional compositions could thus provide a way to analyze non-luminogenic substances or processes through luminescent methods.

BRIEF SUMMARY

In one aspect of the invention, there is a compound of formula (XII)

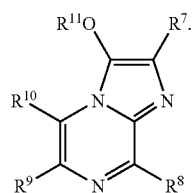

(XII)

In this compound, $R^7$ is H, alkyl, heteroalkyl, aryl, or —$CH_2$—$C_6H_4OR^{14}$; $R^8$ is H, alkyl, heteroalkyl, or aryl; $R^9$ is H, alkyl, heteroalkyl, aryl, or —$C_6H_4OR^{15}$; $R^{10}$ is —H, —$CH_3$, or —$CH(CH_3)_2$; and $R^{11}$, $R^{14}$, and $R^{15}$ are independently enzyme-removable groups; with the proviso that $R^{11}$, $R^{14}$, and $R^{15}$ are not all acetyl groups.

In another aspect of the invention, there is a compound of formula (XII), wherein $R^7$ is H, alkyl, heteroalkyl, aryl, or —$CH_2$—$C_6H_4OR^{14}$; $R^8$ is H, alkyl, heteroalkyl, or aryl; $R^9$ is H, alkyl, heteroalkyl, aryl, or —$C_6H_4OR^{15}$; $R^{10}$ is —H, —$CH_3$, or —$CH(CH_3)_2$; and $R^{11}$, $R^{14}$, and $R^{15}$ are independently enzyme-removable groups. The concentration of this compound in a mixture comprising F12 medium and 10% fetal bovine serum at 22° C. is reduced by less than 50% after 45 minutes.

In yet another aspect of the invention, there is a compound of formula (XII), wherein $R^7$ is H, alkyl, heteroalkyl, aryl, or —$CH_2$—$C_6H_4OR^{14}$; $R^8$ is H, alkyl, heteroalkyl, or aryl; $R^9$ is H, alkyl, heteroalkyl, aryl, or —$C_6H_4OR^{15}$; $R^{10}$ is —H, —$CH_3$, or —$CH(CH_3)_2$; and $R^{11}$, $R^{14}$, and $R^{15}$ are independently enzyme-removable groups. The removal of at least one enzyme-removable group provides a parent compound, and the time necessary for the concentration of this compound in a mixture comprising F12 medium and 10% fetal bovine serum at 22° C. to be reduced by 50% is greater than the time necessary for the concentration of the parent compound in a mixture comprising F12 medium and 10% fetal bovine serum at 22° C. to be reduced by 50%.

In yet another aspect of the invention, there is a compound of formula (XIII) or (XIV)

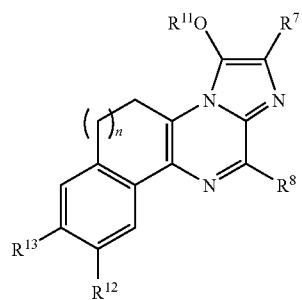

(XIII)

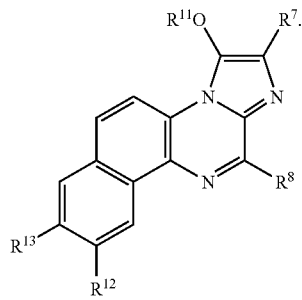

(XIV)

In this compound, $R^7$ is H, alkyl, heteroalkyl, aryl, or —$CH_2$—$C_6H_4OR^{14}$; $R^8$ is H, alkyl, heteroalkyl, or aryl; $R^{12}$ and $R^{13}$ are independently —H, —OH, alkyl, heteroalkyl, aryl, or —$OR^{16}$; n is 0, 1, or 2; and $R^{11}$, $R^{14}$, and $R^{16}$ are independently enzyme-removable groups.

In yet another aspect of the invention, there is a composition comprising one of the above compounds in solution.

In yet another aspect of the invention, there is a protected luminophore, which is a modified coelenterazine, wherein the enol group has been converted to an ester or an ether comprising an enzyme-removable group; the removal of said enzyme-removable group providing a parent coelenterazine. The time necessary for the concentration of the modified coelenterazine in a mixture comprising F12 medium and 10% fetal bovine serum at 22° C. to be reduced by 50% is greater than the time necessary for the concentration of the parent coelenterazine in a mixture comprising F12 medium and 10% fetal bovine serum at 22° C. to be reduced by 50%.

In yet another aspect of the invention, there is a kit comprising a protected luminophore and a luminogenic protein.

In yet another aspect of the invention, there is a kit comprising a protected luminophore and a deprotecting enzyme. The luminophore and the deprotecting enzyme are in separate containers.

In yet another aspect of the invention, there is a method of measuring the enzymatic activity of a luminogenic protein, comprising contacting a luminogenic protein, a deprotecting enzyme, and a protected luminophore in solution to form a composition; and detecting light produced from the composition.

In yet another aspect of the invention, there is a method of generating luminescence in a living cell comprising a luciferase, the method comprising contacting the cell in solution with a protected luminophore.

In yet another aspect of the invention, there is a method of measuring the enzymatic activity of a non-luminogenic enzyme, comprising contacting a non-luminogenic enzyme with a liquid mixture comprising a luminogenic protein and a protected luminophore to form a composition; and detecting light produced from the composition.

DETAILED DESCRIPTION

Figure 1:
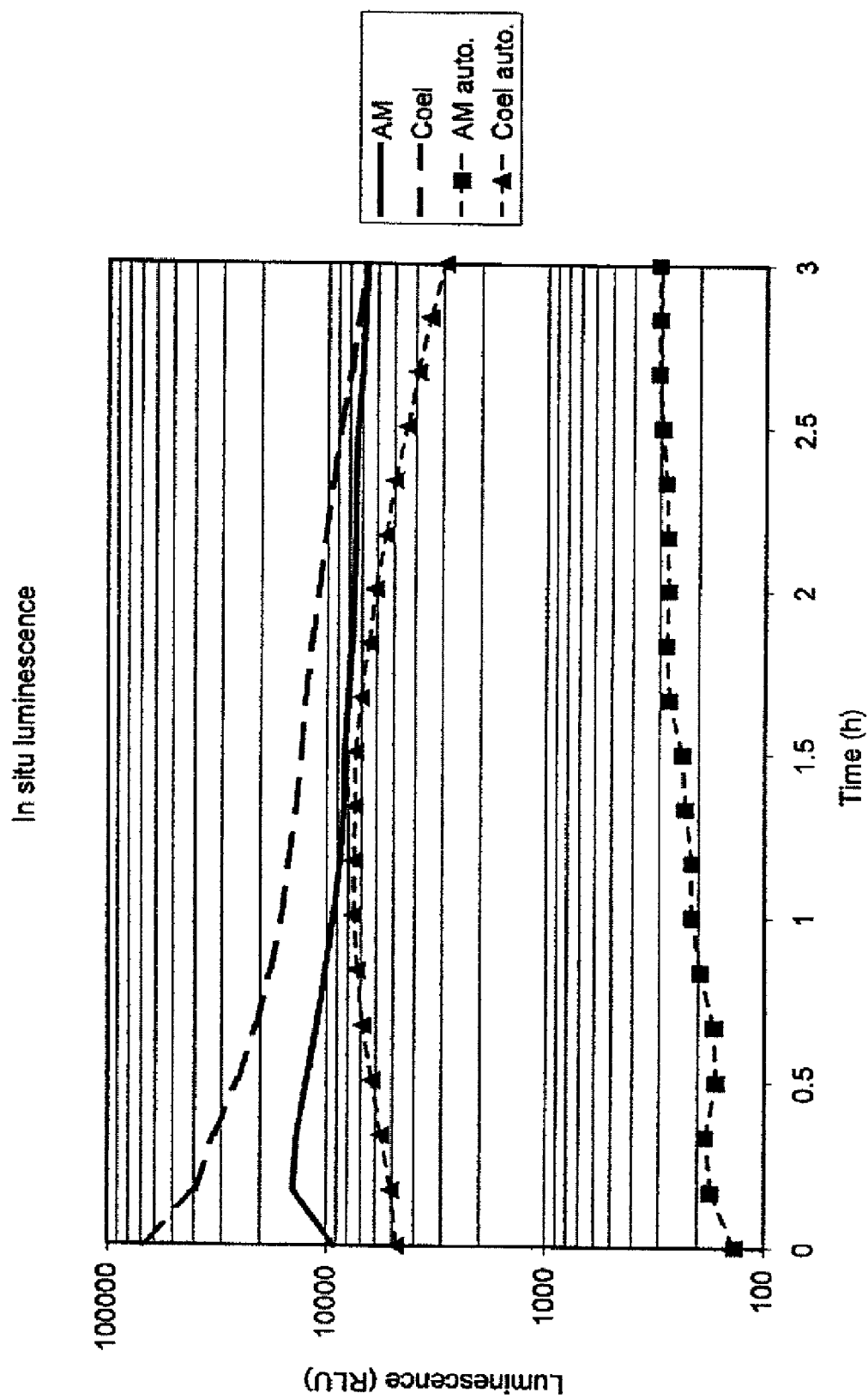
FIG. 1 is a graph of luminescence measured as a function of time.

The present invention provides methods for chemically altering luminophores to yield protected luminophores having greater stability than the unaltered substrate. There is also provided a variety of compositions that can serve as protected luminophores for luminogenic proteins. The protected luminophore can be at least partially converted to the luminophore, allowing the resulting substrate to interact with a luminogenic protein. The protected luminophores provide for decreased autoluminescence, for example in culture medium, without similarly decreasing the luminogenic protein-dependent luminescence within the cell. This effect helps to increase assay sensitivity by increasing the signal-to-background ratio.

The compositions of the present invention are useful in a variety of analytical applications. For in situ applications with cultured cells, the compositions can provide for co-localization of luminophores and luminogenic proteins. The compositions can be used to detect and quantitate luminogenic analytes, which may be either substrates or proteins. The compositions may further be used to detect and quantitate enzymes which convert a protected luminophore into a luminophore. In situ measurements also include analysis of genetic reporters, for example multiplexed reporters where at least one reporter utilizes a luminophore.

For in vivo applications within organisms, the co-localization can provide for studies of cell development. The specificity of a protected luminophore for a non-luminogenic enzyme can be used to measure a luminogenic analyte in a particular organ, tissue or cell type, or to measure the non-luminogenic enzyme in the same. For in vitro applications, it is possible to measure numerous substances and processes over time. These analyses include, for example, the expression of the luminogenic protein, the concentration of analyte, and the expression of the non-luminogenic enzyme which converts the protected luminophore into a luminophore.

Substrates

The luminophores useful for the present invention include a family of compounds referred to as coelenterazines. The term coelenterazine is defined as a molecule with an imidazopyrazine structure, characterized by its ability to luminesce when contacted with a given luminogenic protein in solution. Coelenterazines are known to luminesce when acted upon by a wide variety of luminogenic proteins, specifically marine luciferases. Examples of marine luciferases include *Renilla* luciferase, aequorin, *Gaussia* luciferase, *Oplophorus* luciferase, and *Cypridina* luciferase.

Examples of coelenterazines are given by structures I-III:

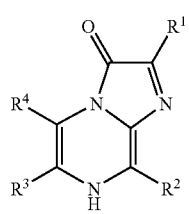
(I)

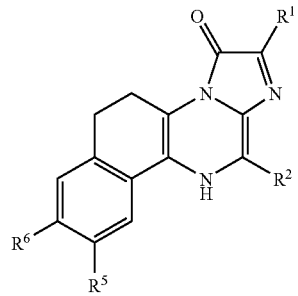
(II)

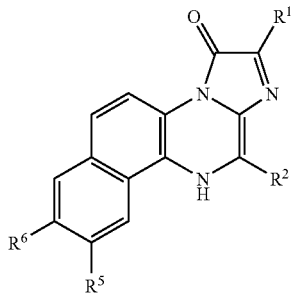
(III)

where $R^1$, $R^2$, $R^3$ and $R^4$ can independently be H, alkyl, heteroalkyl, aryl, or combinations thereof. $R^5$ and $R^6$ can independently be H, OH, alkyl, heteroalkyl, aryl, or combinations thereof. For structure II, n can be 0, 1, or 2, preferably 1.

Preferably, $R^1$ is $-CH_2-C_6H_5$, $-CH_2-C_6H_4OH$, $-CH_2-C_6H_4F$, $-CH(CH_3)CH_2CH_3$, or naphthyl (structure IV-A).

Preferably, $R^2$ is $-CH_2C_6H_5$; $-(CH_2)_3NHC(=N)NH_2$, $-CH_2C_6H_{11}$ (structure IV-B); or $-CH_2C_5H_9$ (structure IV-C).

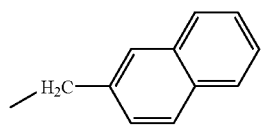
(IV-A)

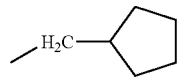
(IV-B)

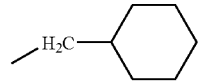
(IV-C)

Preferably, $R^3$ is $-C_6H_4OH$, $-C_6H_4NH_2$, $-C_6H_5$, $-C_6H_4F$, or indolyl (structure V).

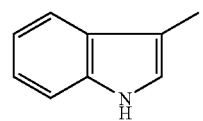
(V)

Preferably, $R^4$ is H, $CH_3$, or $CH(CH_3)_2$.
Preferably, $R^5$ and $R^6$ are independently H or OH.

As used herein, "alkyl" is a hydrocarbon chain containing from 1 to 20 carbon atoms, preferably from 1 to 15 carbon atoms, which may be straight, branched, or cyclic; for example, —$CH_3$, —$CH_2(CH_2)_nCH_3$, —$(CH_2)_nCH(CH_3)_2$, —$(CH_2)_nC(CH_3)_3$ (where n is an integer), adamantyl, and structures IV-B and IV-C.

"Heteroalkyl" is an alkyl group which also contains one or more heteroatoms such as O, N, S and halogen; for example —$(CH_2)_n$—O—$(CH_2)_mCH_3$, —$(CH_2)_n$—C(=O)—N$(CH_3)_2$, —$(CH_2)_3NHC(=N)NH_2$, and —$(CH_2)_n$—C(=O)OH where n and m are integers.

"Heterocycle" is a hydrocarbon containing from 2 to 30 carbon atoms and at least one heteroatom (O, N, or S) such that a ring is formed which contains the heteroatom. The ring may be saturated, partially unsaturated, or aromatic, and may be substituted. The ring may be mono-, bi-, or polycyclic. Examples include acridine, benzathiazoline, benzimidazole, benzofuran, benzothiophene, benzothiazole, benzothiophenyl, carbazole, cinnoline, furan, imidazole, 1H-indazole, indole, isoindole, isoquinoline, isothiazole, morpholine, oxazole (i.e. 1,2,3-oxadiazole), phenazine, phenothiazine, phenoxazine, phthalazine, piperazine, pteridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, triazole (i.e. 1,2,3-triazole), and the like.

"Aryl" is a hydrocarbon containing from 6 to 30 carbon atoms and at least one aromatic carbocyclic group, optionally having substituents containing heteroatoms such as O, N, S, and halogen; for example, —$C_6H_5$ (phenyl), —$C_6H_4OH$, —$C_6H_4$—$C_6H_5$, —$C_9H_7$, —$C_6H_4OCH_3$, —$C_6H_4NH_2$, —$C_6H_4SH$, —$CH_2$—$C_6H_5$, and naphthyl.

Coelenterazines, including natural coelenterazine and modified colenterazines, are available from PROMEGA CORPORATION, Madison, Wis. and from MOLEUCLAR PROBES, INC., Eugene, Oreg. Coelenterazines may also be synthesized as described for example in Shimomura et al., *Biochem. J.* 261: 913-20, 1989; Inouye et al., *Biochem. Biophys. Res. Comm.* 233: 349-53, 1997; and Teranishi et al., *Anal. Biochem.* 249: 37-43, 1997.

Both natural coelenterazine and modified coelenterazines are broadly referred to herein as "coelenterazines" and function as luminophores with luminogenic proteins. Specific examples of these luminophores include those based on structure I as outlined in Table A as well as those based on structures II and III as outlined in Table B. Coelenterazines having structures VI, commonly referred to as "coelenterazine," VII, commonly referred to as "coelenterazine-h", and VIII, commonly referred to as "dideoxycoelenterazine", correspond to the first, second, and third entries in Table A respectively.

TABLE A

| $R^1$ | $R^2$ | $R^3$ | $R^4$ |
|---|---|---|---|
| —$CH_2$—$C_6H_4$—OH | —$CH_2$—$C_6H_5$ | —$C_6H_4$—OH | H |
| —$CH_2$—$C_6H_5$ | —$CH_2$—$C_6H_5$ | —$C_6H_4$—OH | H |
| —$CH_2$—$C_6H_5$ | —$CH_2$—$C_6H_5$ | —$C_6H_5$ | H |
| —$CH_2$—$C_6H_4$—F | —$CH_2$—$C_6H_5$ | —$C_6H_4$—OH | H |
| —$CH_2$—(2-naphthyl) | —$CH_2$—$C_6H_5$ | —$C_6H_4$—OH | H |
| —$CH_2$—$C_6H_5$ | —$CH_2$—cyclopentyl | —$C_6H_4$—OH | H |
| —$CH_2$—$C_6H_4$—OH | —$CH_2$—cyclopentyl | —$C_6H_4$—OH | H |
| —$CH_2$—$C_6H_3$(F)(F) | —$CH_2$—$C_6H_5$ | —$C_6H_4$—OH | H |

TABLE A-continued

| R¹ | R² | R³ | R⁴ |
|---|---|---|---|
| —CH₂—C₆F₅ | CH₂-phenyl | 4-hydroxyphenyl | H |
| CH₂-(4-Cl-phenyl) | CH₂-phenyl | 4-hydroxyphenyl | H |
| CH₂-(4-Br-phenyl) | CH₂-phenyl | 4-hydroxyphenyl | H |
| CH₂-(4-I-phenyl) | CH₂-phenyl | 4-hydroxyphenyl | H |
| CH₂-(4-OH-phenyl) | n-pentyl | 4-hydroxyphenyl | H |
| CH₂-(4-OH-phenyl) | isobutyl | 4-hydroxyphenyl | H |
| CH₂-(4-OH-phenyl) | CH₂-cyclohexyl | 4-hydroxyphenyl | H |
| CH₂-(4-OH-phenyl) | CH₂CH₂-cyclohexyl | 4-hydroxyphenyl | H |
| CH₂-(4-OH-phenyl) | CH₂CH₂-phenyl | 4-hydroxyphenyl | H |
| CH₂-(4-OH-phenyl) | CH₂-(4-F-phenyl) | 4-hydroxyphenyl | H |
| CH₂-(4-F-phenyl) | n-pentyl | 4-hydroxyphenyl | H |
| CH₂-(4-F-phenyl) | isobutyl | 4-hydroxyphenyl | H |
| CH₂-(4-F-phenyl) | CH₂-cyclopentyl | 4-hydroxyphenyl | H |
| CH₂-phenyl | CH₂-cyclohexyl | 4-hydroxyphenyl | H |
| CH₂-(4-F-phenyl) | CH₂-cyclohexyl | 4-hydroxyphenyl | H |
| CH₂-(4-OH-phenyl) | CH₂-phenyl | 4-hydroxyphenyl | CH₃ |

TABLE A-continued

| R¹ | R² | R³ | R⁴ |
|---|---|---|---|
| -CH₂-cyclohexyl | -CH₂-phenyl | -C₆H₄-OH (para) | H |
| -CH(CH₃)CH(CH₃)₂ (sec-butyl-like) | -CH₂-phenyl | -C₆H₄-OH (para) | H |
| -CH₂-C₆H₄-OH (para) | -CH₃ | -C₆H₄-OH (para) | H |
| -CH₂-C₆H₄-OH (para) | -CH₂-phenyl | -C₆H₄-F (para) | H |
| -CH₂-C₆H₄-OH (para) | -CH₂-phenyl | -C₆H₄-OH (meta) | H |
| -CH₂-(4-biphenyl) | -CH₂-phenyl | -C₆H₄-OH (para) | H |
| -(CH₂)₂-phenyl | -CH₂-phenyl | -C₆H₄-OH (para) | H |
| -(CH₂)₃-phenyl | -CH₂-phenyl | -C₆H₄-OH (para) | H |
| -CH₂-C₆H₄-OH (para) | -CH₂-phenyl | -C₆H₄-NH₂ (para) | H |
| -CH₂-C₆H₄-OH (para) | -CH₂-phenyl | -C₆H₄-NHCH₃ (para) | H |
| -CH₂-C₆H₄-OH (para) | -CH₂-phenyl | -C₆H₄-OCH₃ (para) | H |
| CH₃ | H | -C₆H₄-OCH₃ (para) | H |
| CH₃ | -CH₂-phenyl | -C₆H₄-OCH₃ (para) | CH₂CH₃ |
| CH₃ | -CH₂-phenyl | -C₆H₄-OCH₃ (para) | H |
| CH₂—(CH₃)₃ | -CH₂-phenyl | -C₆H₄-OCH₃ (para) | H |

TABLE A-continued

| R¹ | R² | R³ | R⁴ |
|---|---|---|---|
| -(CH₂)₂-COOH | -CH₂-C₆H₅ | -C₆H₄-OCH₃ | H |
| -(CH₂)₂-C(O)-N(CH₃)₂ | -CH₂-C₆H₅ | -C₆H₄-OCH₃ | H |
| CH₃ | -CH₂-C₆H₅ | -C₆H₄-OCH₃ | CH₃ |
| CH₂-(CH₃)₃ | -CH₂-C₆H₅ | -C₆H₄-OCH₃ | CH₃ |
| CH₂-(CH₃)₃ | H | -C₆H₄-OCH₃ | H |
| CH₃ | -CH₂-C₆H₅ | -C₆H₄-OCH₃ | -CH(CH₃)₂ |
| CH(CH₃)CH₂CH₃ | -(CH₂)₃-NH-C(=NH)-NH₂ | 3-methyl-1H-indol-yl | H |
| -(CH₂)₂-C(O)-NH-(α-CD) | H | -C₆H₄-OCH₃ | H |
| -(CH₂)₂-C(O)-NH-(β-CD) | H | -C₆H₄-OCH₃ | H |
| -(CH₂)₂-C(O)-O-(2,4-diCl-C₆H₃) | -CH₂-C₆H₅ | -C₆H₄-OCH₃ | H |

* CD = cyclodextrin

TABLE B

Structure II

| R¹ | R² | R⁵ | R⁶ | N |
|---|---|---|---|---|
| -CH₂-C₆H₄-OH | -CH₂-C₆H₅ | OH | H | 1 |
| -CH₂-C₆H₅ | -CH₂-C₆H₅ | OH | H | 1 |
| -CH₂-C₆H₄-F | -CH₂-C₆H₅ | OH | H | 1 |
| -CH₂-C₆H₄-OH | -CH₂-C₆H₁₁ | OH | H | 1 |

TABLE B-continued

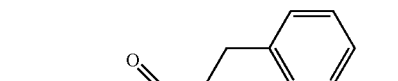

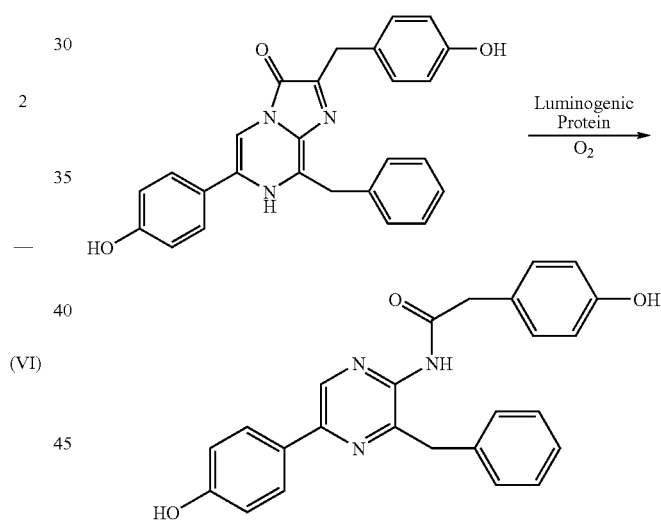

Coelenterazines can function as luminophores for a variety of luminogenic proteins. Factors which affect this interaction include the identity of the luminogenic protein and the characteristics of the surrounding environment. For example, the interaction of a luminogenic protein, such as *Renilla* or *Oplophorus* luciferase or aequorin, with a coelenterazine, in the presence of $O_2$ and at least a trace of cofactor $Ca^{2+}$, will produce luminescence. The coelenterazine is oxidized to its corresponding coelenteramide during this process, as illustrated below.

The luminescence that results from these interactions can be measured and, in some systems, correlated with the amount of protein, coelenterazine, and/or cofactor involved. Luminescence measurements are typically carried out by integrating the intensity of light that is emitted from a sample having a given surface area. Instruments which are useful for measuring luminescence include luminometers, charge-coupled devices (CCD), and photomultiplier tubes.

Protected Luminophores

Protected luminophores can increase the utility of luminescent assays. "Protected luminophore" is defined as a coelenterazine which has been modified such that it will no longer interact with a luminogenic protein to luminesce. If the modification is the addition of an enzyme-removable group to the coelenterazine, then interaction of the protected luminophore with an appropriate enzyme yields an active coelenterazine capable of luminescence. The enzyme which converts the protected luminophore into a luminophore is preferably a non-luminogenic enzyme. All of the coelenterazines mentioned above may be converted into protected luminophores. The term "group" refers to any part of a chemical compound.

Generally, this derivatization involves the conversion of functional groups such as phenol (—$C_6H_4$—OH), carbonyl (>C=O), and aniline (—$C_6H_4$—$NH_2$) into groups which are less reactive toward their surroundings. Since the normal reactivities of the functional groups are inhibited by the presence of the enzyme-removable group, the enzyme-removable group can be referred to as a protecting group. Possible protecting groups include esters, which can be removed by interaction with esterases. Possible protecting groups also include phosphoryls, which can be removed by interaction with phosphatases, including phosphodiesterases and alkaline phosphatase. Possible protecting groups also include glucosyls, which may be removed by interaction with glycosidases, α-D-galactoside, β-D-galactoside, α-D-glucoside, β-D-glucoside, α-D-mannoside, β-D-mannoside, β-D-fructofuranoside, and β-D-glucosiduronate. One skilled in the art would be able to recognize other enzyme-removable protecting groups that could be used in the invention. Examples of the interaction of enzymes and enzyme-removable groups are described in U.S. Pat. No. 5,831,102, as well as Tsien, R. Y. *Nature*, 290: 527-28, 1981; Redden, P. R. et al., *Int J Pharm*, 180: 151-60, 1999; and Annaert, P. et al., *Pharmaceut Res*, 14: 492-96, 1997.

Enzyme-removable groups may be designed such that they can only be removed by the action of a specific enzyme. For example, certain fatty acids may be used as enzyme-removable groups, and only specific esterases will convert these protected luminophores into luminophores. A protecting group with high steric hindrance, such as a tert-butyl group, may be used. Such a protecting group could be useful in screening for novel esterases that can act upon bulky, hindered esters. Amino acids may also be used as protecting groups. The protected luminophores may be further modified by substituting the enol oxygen atom with a nitrogen atom connected to a protecting group. This type of protecting group could then be removed by a protease, and subsequent hydrolysis of the protected luminophore to the enol/carbonyl would provide a luminophore.

These enzyme-removable groups are preferably derivatives of alcohol functional groups. In the case of a carbonyl functional group in coelenterazines, derivatization may involve the conversion of the carbonyl to an enol group (—C=C—OH). The carbonyl and enol forms of the coelenterazine may be in a dynamic equilibrium in solution such that there is always a proportion of the substrates that are in the enol form. The hydroxyl (—OH) portion of the enol group can be derivatized. Derivatization via ester formation using an acylating agent is illustrated schematically below. The coelenterazine having structure VI contains two phenolic groups and one carbonyl group, and any combination of these groups may be protected.

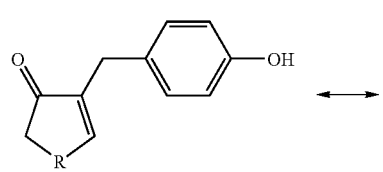

-continued

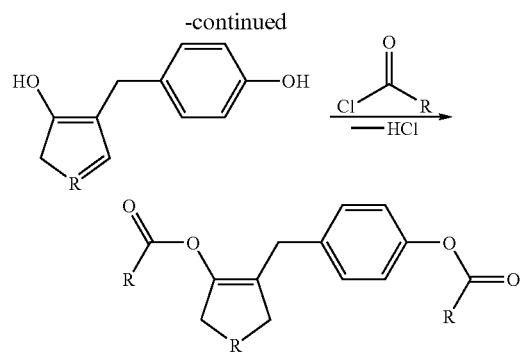

Derivatization with ether protecting groups can be carried out for example by treating the coelenterazine with an alkylating agent such as acetoxymethyl bromide. Derivatization with ester protecting groups can be carried out for example by treating the coelenterazine with an acylating agent, such as an acetic anhydride or an acetyl chloride. These derivatizations are carried out in basic conditions, that is pH between 7 and 14. Under these conditions, both the phenolic hydroxyls as well as the imidazolone oxygen can react to form the corresponding esters or ethers. The imidazolone oxygen is believed to react when in the form of the enol. Examples of the protection/deprotection process as well as various protecting groups are described in "Protective Groups in Organic Synthesis." Eds. Greene, Wuts. John Wiley and Sons, New York, 1991.

One example of the derivatization process is the synthesis of protected luminophore IX from coelenterazine VI. Protected luminophore IX is also known as triacetyl-coelenterazine due to the presence of three acetyl protecting groups.

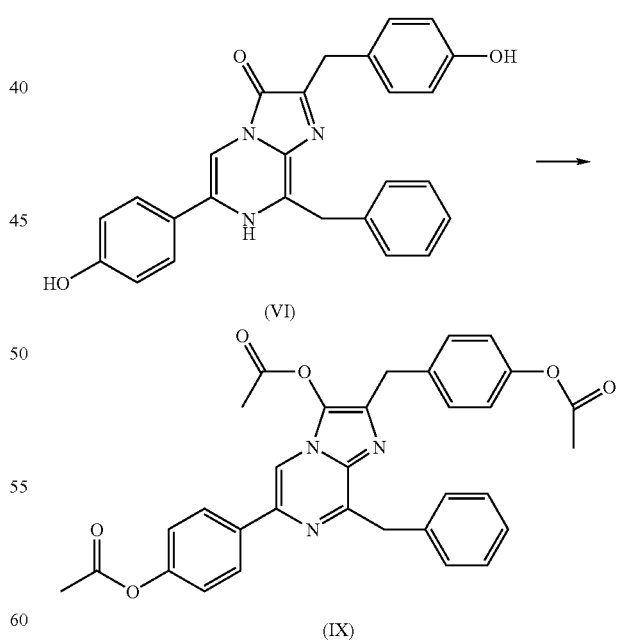

A compound having the structure of compound IX has reportedly been used as in intermediate in efforts to establish the structure of native coelenterazine VI (Inoue et al. *Tetrahedron Letters* 31: 2685-2688 (1977)). It is expected that protected luminophore IX would have fairly low stability relative to other protected luminophores, given the lability of the acetyl-derivatized enol group.

For a given protecting group, a derivatized enol is more labile than a similarly derivatized phenol. This increased ability of the enol derivative to react permits the selective hydrolysis of the enol derivative to again provide the imidazolone carbonyl. This type of compound is referred to as a partially protected species since some of the functional groups are protected while others are not. These partially protected species can be used in biological assays, or they can be further reacted with a different acylating or alkylating agent to form an unsymmetrical compound, that is a compound with more than one type of protecting group. Selection of the appropriate protecting group may depend on the cell type under consideration and on the desired rate of hydrolysis. The selective hydrolysis can be carried out, for example, as described in Inoue et al., *Tetrahedron Letters* 31: 2685-88, 1977. This is illustrated in the following reaction scheme, for the selective hydroysis of triacetyl-coelenterazine (IX) to diacetyl-coelenterazine (X) and subsequent formation of an unsymmetrical protected luminophore (XI).

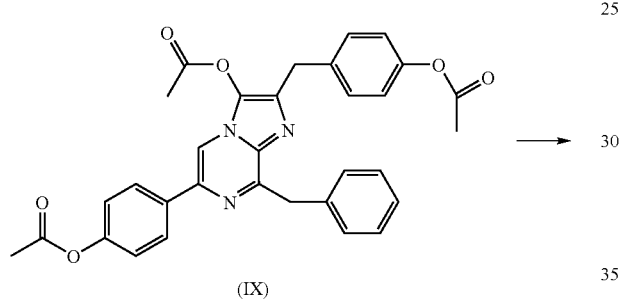

Structures XII-XIV illustrate protected luminophores having a protecting group on the carbonyl.

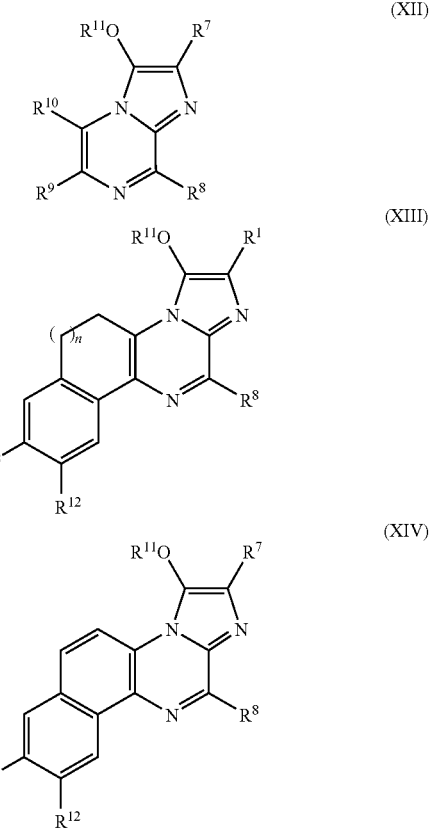

$R^7$, $R^8$, $R^9$ and $R^{10}$ can independently be H, alkyl, heteroalkyl, aryl, or combinations thereof. $R^{12}$ and $R^{13}$ can independently be —$OR^{16}$, H, OH, alkyl, heteroalkyl, aryl, or combinations thereof. For structure XIII, n can be 0, 1, or 2, preferably 1.

Preferably, $R^7$ is as described for $R^1$ or is —$CH_2$—$C_6H_4OR^{14}$.

Preferably $R^8$ is as described for $R^2$, and $R^{10}$ is as described for $R^4$.

Preferably, $R^9$ as described for $R^3$ or is —$C_6H_4OR^{15}$.

$R^{11}$, $R^{14}$, $R^{15}$, and $R^{16}$, together identified as $R^P$, are protecting groups and can be independently any of a variety of protecting groups. Preferably, these species, together with their corresponding O atom, are ethers, esters, or combinations thereof. For example, the protecting group can be acetyl ($R^P$=—C(=O)—$CH_3$), butyryl ($R^P$=—C(=O)—$C_3H_7$), acetoxymethyl ($R^P$=—$CH_2$—O—C(=O)—($CH_3$)), propanoyloxymethyl ($R^P$=—$CH_2$—O—C(=O)—$C_2H_5$), butyryloxymethyl ($R^P$=—$CH_2$—O—C(=O)—$C_3H_7$), pivaloyloxymethyl ($R^P$=—$CH_2$—O—C(=O)—$C(CH_3)_3$), or t-butyryl ($R^P$=—C(=O)—$C(CH_3)_3$).

Specific examples of protected luminophores include triacetyl-coelenterazine (IX), tributyryl-coelenterazine (XV), diacetyl-coelenterazine-h (XVI), acetoxymethyl diacetyl-coelenterazine (XVII), acetoxymethyl acetyl-coelenterazine-h (XVIII), pivaloyloxymethyl-coelenterazine-h (XIX), and acetoxymethyl-dideoxycoelenterazine (XX).

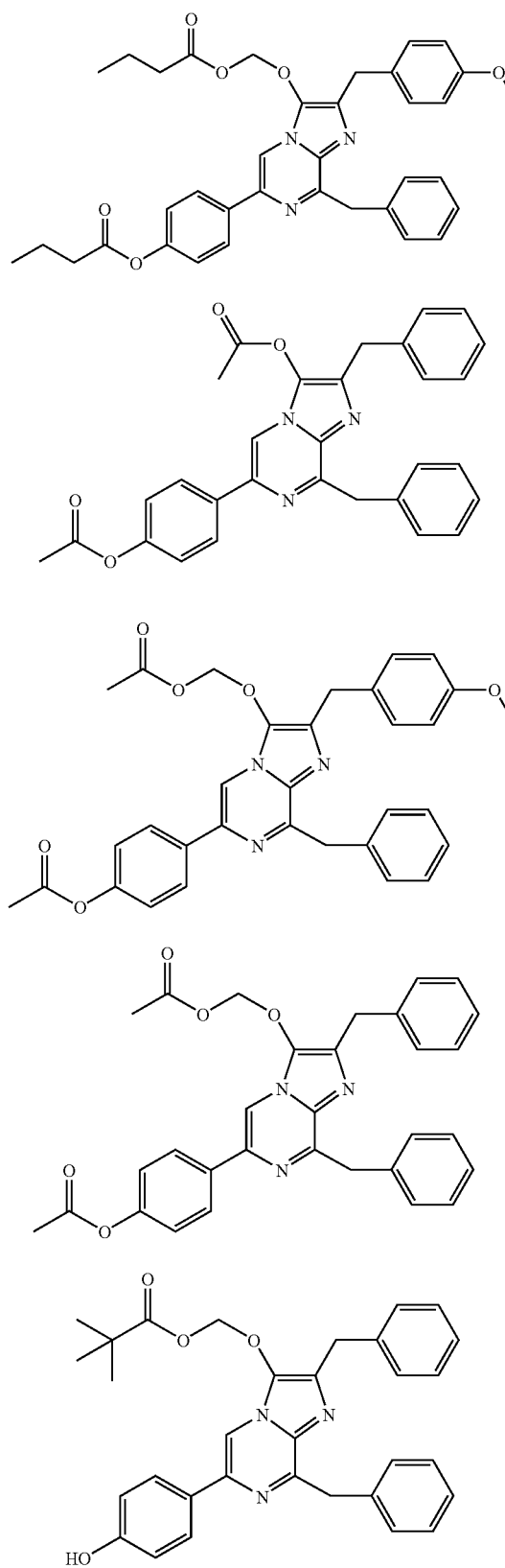

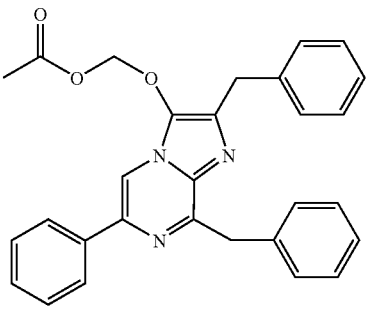

The protecting groups can be removed, and the original functional group restored, when the protected luminophore interacts with the appropriate deprotecting enzyme. For ester and ether protecting groups, the deprotecting enzyme can for example be any hydrolase, including esterases. For coelenterazines, having the carbonyl functional group in its deprotected form (ie. carbonyl) allows for a luminescent interaction with a luminogenic protein, including *Renilla* luciferase, *Oplophorus* luciferase, *Cypridina* luciferase, and aequorin. The protected luminophore may only need to be deprotected at the carbonyl site to be converted into a luminophore. The presence of protecting groups on the phenolic hydroxyls may still hinder or prevent a luminescent interaction, however.

Properties of Protected Luminophores

The protected luminophores exhibit increased stability under normal use conditions relative to their corresponding luminophores. Coelenterazines are typically unstable when solvated, particularly in aqueous solutions above neutral pH (e.g., cell culture medium), and this instability can lead to autoluminescence. Autoluminescence contributes to the measured background in the system, reducing the sensitivity of the measurement. Also, this instability can cause the duration of the signal to be relatively short. This duration can be quantified by the half-life of the signal, which is defined as the time necessary for the signal to decline to half its original magnitude.

"Stability" for both protected luminophores and luminophores is defined as the half-life of the particular compound in a specific environment. The half-life is the time necessary for the concentration of the compound to be reduced to half its initial value. The presence and/or concentration of a particular compound can be determined by a variety of techniques known to those skilled in the art. These techniques include, for example, nuclear magnetic resonance (NMR) and high performance liquid chromatography (HPLC). Preferably, stability is tested by first mixing a protected luminophore or a luminophore with an aqueous mixture to give an initial concentration. This aqueous mixture is preferably F12 medium containing 10% fetal bovine serum at a temperature of 22° C. Small aliquots are then removed from the mixture at certain time intervals, and the concentration of the compound is determined by HPLC. The time required for the measured concentration to fall to 50% of the initial concentration is the half-life. A longer half-life corresponds to a more stable compound.

The protected luminophores of the present invention are more stable than their corresponding luminophores. In comparing stabilities, the luminophore is referred to as a "parent compound" to the protected luminophore, since all enzyme-removable groups have been removed. Other "parent compounds" to the protected luminophore are the partially deprotected derivatives. That is, parent compounds include protected luminophores which have had at least one enzyme-removable group removed. For example, both compounds VI and X are parent compounds to compound IX.

The remarkable stability of the protected luminophores provides for a variety of enhancements of luminogenic assays. For example, the protected luminophores do not luminesce when contacted with a luminogenic protein, but must first interact with an appropriate deprotecting enzyme. Thus, the protected luminophore can be converted into a luminophore in close proximity to the luminogenic protein. The luminophore, which is less stable than the protected luminophore, is protected from destabilization (i.e. autoluminescence), since it is not in its active form until after the interaction with the deprotecting enzyme. If the deprotecting enzyme is confined to a particular area in a cell or an organism, then it is possible to detect luminescence only in that area.

The use of protected luminophores in luminescent assays can provide many other advantages, including an increase in the signal-to-background ratio of the assay and improved stability of the luminescent signal.

Assays: in vitro

In certain embodiments of the present invention, the protected luminophores may be used as assay reagents. Assays using luciferases are well known in the art. Such assays are particularly useful for analyzing biological mechanisms, such as gene expression and regulation. Typically, cells are transfected with a nucleic acid encoding a luciferase, then lysed to produce a protein extract. The presence of luciferase in the protein extract is determined by the addition of reagents, including substrate.

In preferred embodiments, a protected luminophore is used in an assay comprising *Renilla* luciferase. *Renilla* luciferase may be the sole light producing protein in the assay (Srikantha et al., *J. Bacteriol.* 178(1):121-9, 1996; Liu and Escher, *Gene* 237(1):153-9, 1999), may be present with one or more other light producing proteins (Skarpidi et al., *Blood* 96(1): 321-6, 2000; Parsons et al., *Anal. Biochem.* 281(2):187-92, 2000; Stables et al., *J. Recept. Signal Transduct. Res.* 19(1-4):395-410, 1999; Grentzmann et al., *RNA* 4(4):479-86, 1998), or may be part of a fusion protein with another light producing protein (Liu et al., *Luminescence* 15(1):45-9, 2000).

In some embodiments, a protected luminophore is used in an assay wherein a deprotecting enzyme is present in a sample prior to the addition of the assay reagents. Such assays may be useful in methods of determining the presence of a deprotecting enzyme in a sample. For example, *Renilla* luciferase and protected luminophore may be added to a sample. If deprotecting enzyme is present in the sample, the protected luminophore will be activated and available to the luciferase producing light. If deprotecting enzyme is not present, the protected luminophore remains unavailable to the luciferase and light is not produced. Such assays also are useful in determining relative concentrations of the deprotecting enzyme in a sample.

In other embodiments, the deprotecting enzyme is included in an assay reagent. For example, in a dual luciferase assay comprising beetle and *Renilla* luciferases, ATP, luciferin, and a protected luminophore may be first added to a sample. The beetle luciferase will utilize the ATP and luciferin, and the light produced is measured. A deprotecting enzyme is subsequently added. The deprotecting enzyme activates the coelenterazine by removing at least the protecting group from the enol/carbonyl group. The substrate thus has a carbonyl group which is capable of participating in the coelenterazine-*Renilla* luciferase luminescent interaction, and the light produced is detected.

In alternative embodiments, using beetle and *Renilla* luciferases, the assays are used to detect or quantify cells in a sample. Because beetle luciferase is dependent on ATP for activity, it is used to detect ATP in a sample. This dependence has been taken advantage of to produce ATP assays, cell detection assays, and cell viability assays using beetle luciferase. Using a single dual-luciferase assay with a protected luminophore, the presence in a sample of ATP and the deprotecting enzyme can be determined.

Assays: in situ

The compounds of the present invention are particularly useful in in situ methods of analyzing cells. Methods of performing in situ analysis of cells using a luciferase are known in the art, see U.S. Pat. No. 5,998,204. The protected luminophores of the present invention require removal of the protecting group to become substrate for the luciferase. However, once the protecting group is removed the compounds may be immediately used as substrate by a luciferase. Thus, it may be determined where the deprotecting enzyme is located in a cell by in situ imaging. This may be done by contacting a cell expressing a luciferase, such as *Renilla* luciferase, with a protected luminophore. Wherever an enzyme that is capable of deprotecting the protected luminophore is located in the cell, a glow will occur. This glow may be detected by an imaging system. Protected luminophores are also useful in analysis of reporter gene expression. The production of the deprotecting enzyme required to convert the protected luminophore into a luminophore may be affected by a variety of factors. Since the presence and amount of the deprotecting enzyme can be determined through the use of the protected luminophore, the expression of the enzyme can be studied.

Using bioluminescence resonance energy transfer (BRET), it can be determined if two molecules are capable of binding each other or are co-localized in a cell (Angers et al., Proc. Natl. Acad. Sci. U.S.A. 97(7):3684-9, 2000). BRET involves the use of either two bioluminescent molecules or one bioluminescent molecule and one fluorescent molecule. The molecules are chosen such that the emission wavelength of the donor is within the excitation spectra of the acceptor. Furthermore, the excitation and emission spectra of the two molecules should overlap minimally if at all. When the molecules are in close proximity to each other, excitation of the donor leads to a transfer of the energy to the acceptor rather than an emission of light. The acceptor then emits the transferred energy as light. Thus, when the molecules are in close proximity to each other, light detected from the donor is low, while light detected from the acceptor is high. When the molecules are not in close proximity to each other, light detected from the donor is high, while light detected from the acceptor is low (PCT Publication WO99/66324).

By linking the donor to a first protein and the acceptor to a second protein, interaction of the two proteins can be determined by the detection of BRET. (Angers et al., 2000). In preferred embodiments, the donor is *Renilla* luciferase and the acceptor is green fluorescent protein. When protected luminophore is used in such assays, the accuracy of the assays are greatly increased because of the reduction of light produced by destabilization of luminophore.

The analysis of biochemical processes is not limited to in vitro or in situ environments, but can be extended to in vivo studies. Applications of the protected luminophores to in vivo luminescent analysis will be readily apparent to those skilled in the art.

Kits

An important aspect of the present invention includes kits comprising the protected luminophores of the present invention. A kit may be provided for essentially any assay wherein a luminophore is used, including the preferred methods described in detail herein. In preferred embodiments, the essential reagents for a particular assay are provided by the kit. Such reagents may include thiourea or a thiourea derivative, one or more aqueous buffers, and enzymes. Reagents may also include DMSO and/or alcohol to help solubilize the protected luminophore. Each reagent may have its own container or several reagents may be pre-mixed and packaged together in a container. In certain embodiments, the kit comprises a gene encoding a luciferase. In other embodiments, the luciferase protein itself is provided.

Compounds

The present invention also provides novel compounds of formulas XII, XIII, and XIV. For compound XII, and $R^7$ is —$CH_2$—$C_6H_4OC(=O)CH_3$ and $R^9$ is —$C_6H_4OC(=O)CH_3$, $R^{10}$ is H, and $R^8$ is —$CH_2C_6H_5$, then $R^{11}$ is not —$C(=O)CH_3$. Preferably, the present invention provides novel compounds of formulas XII, XIII, and XIV which further have half-lives in a mixture of F12 medium and 10% fetal bovine serum at 22° C. of at least 45 minutes. Preferably, protected luminophores of formulas XII, XIII, and XIV are more stable than their parent compounds, as measured by the half-life of the compounds in an aqueous environment. Specifically, the present invention provides novel compounds of formulas XV, XVI, XVII, XVIII, XIX, and XX.

EXAMPLES

All solvents and reagents were obtained from FISHER SCIENTIFIC except as follows. Mathew's Buffer was assembled from the following, obtained from SIGMA CHEMICALS: 100 mM potassium phosphate buffer, pH 7.4; 500 mM sodium chloride; 1 mM ethylenediamine tetraacetic acid (EDTA); and 0.1% w:v Gelatin Type A (75-100 Bloom). Ham's F12 medium and fetal bovine serum were obtained from LIFE TECHNOLOGIES, Rabbit esterase was obtained from SIGMA CHEMICALS, and *Renilla* luciferase was obtained from CHEMICON CORP.

Example No. 1

In this example, a protected luminophore bearing three acetyl protecting groups was synthesized from a coelenterazine having the structure VI. To a solution of compound VI (STOP AND GLO® SUBSTRATE, PROMEGA CORPORATION) (500 mg; 1.2 mM) in anhydrous pyridine (20 ml) was added acetic anhydride (1.1 ml; 12 mM), and the reaction was kept under an inert atmosphere at room temperature. After 1 hour, 30 ml of $CH_2Cl_2$ was added to the reaction, followed by 80 ml $H_2O$. This mixture was stirred for 5 minutes, and then the layers were separated. The organic layer was evaporated to dryness and then purified by column chromatography as follows. Normal phase silica (20 g) was solvated in $CH_2Cl_2$ and loaded into an appropriate sized glass column. The extracted reaction mixture was taken up in a minimum of $CH_2Cl_2$ and applied to the top of the column. A step gradient was employed, starting at 1% ethyl acetate (EtOAc) in $CH_2Cl_2$ and increasing in polarity until the desired compound eluted (10% EtOAc in $CH_2Cl_2$). All fractions that appeared clean by HPLC (>95%) were pooled and evaporated to dryness to yield 410 mg of pure compound IX.

Example No. 2

In this example, a protected luminophore bearing three butyryl protecting groups was synthesized from a coelenterazine having the structure VI. To a solution of compound VI (300 mg; 0.7 mM) in anhydrous pyridine (30 ml) was added butyric anhydride (1.12 g; 7 mM), and the reaction was allowed to sit under an inert atmosphere at room temperature. After 1 hour, the reaction mixture was placed under vacuum in order to remove the solvent until a syrup was formed. To the syrup was added 30 ml $CH_2Cl_2$, followed by 80 ml $H_2O$. This mixture was stirred for 5 minutes, and then the layers were separated. The organic layer was then evaporated to dryness and then purified by column chromatography as follows. Normal phase silica (20 g) was solvated with 2% EtOAc in $CH_2Cl_2$ and loaded into an appropriate sized glass column. The extracted reaction mixture was taken up in minimum of $CH_2Cl_2$ and applied to the top of the column. The mobile phase was isocratic, and all of the desired compound eluted with 2% EtOAc in $CH_2Cl_2$. All fractions that appeared clean by HPLC (>95%) were pooled and evaporated to dryness to yield 225 mg of pure compound XV.

Example No. 3

In this example, a coelenterazine having structure VII was synthesized. The synthesis procedure was a modification of that reported by Inoue et al. (Inoue and Kakoi, *Heterocycles* 48(8), 1669 (1998)). To a solution of 2-amino-3-benzyl-5(4-hydroxyphenyl)pyrazine (2 g, 7.2 mM) in xylenes (80 mL) was added phenylpyruvic acid (8.3 g, 50.5 mM) all at once, and the reaction mixture was heated at reflux (130-140° C.) for 1 hr and then cooled to room temperature. The mixture was evaporated under reduced pressure to a dark solid foam. This foam was separated by chromatography on 300 g of N.P. silica with step gradient of methanol in $CH_2Cl_2$. The desired product eluted with 5% methanol in $CH_2Cl_2$ to yield 2 g of compound VII, which was 80% pure by HPLC. This chromatography was repeated to yield 900 mg of compound VII ("coelenterazine-h", >95% by HPLC) as a brown solid.

Example No. 4

In this example, a protected luminophore bearing two acetyl protecting groups was synthesized from a coelenterazine having the structure VII. To a solution of compound VII (300 mg; 0.74 mM) in anhydrous pyridine (15 ml) was added acetic anhydride (1 ml; 11 mM), and the reaction was allowed to sit under an inert atmosphere at room temperature. After 1 hour, the reaction mixture was evaporated to a viscous syrup and this syrup was purified by column chromatography as follows. Normal phase silica (40 g) was solvated with a 1:3 mixture of EtOAc and heptane and loaded into an appropriate sized glass column. The syrup was taken up in a minimum of $CH_2Cl_2$ and applied to the top of the column. The mobile phase was isocratic, and all of the desired compound eluted with 1:3 EtOAc/heptane. All fractions that appeared clean by HPLC (>95%) were pooled and evaporated to dryness to yield 170 mg of pure compound XVI.

Example No. 5

In this example, a protected luminophore bearing one acetyl protecting group (on the phenol group) was synthesized from the protected luminophore (XVI) synthesized in Example 4. A 1% solution of compound XVI in a 1:1 mixture of pyridine and $CH_2Cl_2$ was cooled to 0° C. To this solution, a pre-cooled 1% solution of methanolic ammonia was added dropwise. The volume of the ammonia solution was equivalent to the volume of pyridine/$CH_2Cl_2$ mixture that was used to dissolve XVI. After a few minutes of reaction, an aliquot was examined by HPLC to determine the degree of completion of the deprotection. By HPLC, a new peak formed that is more polar (ie. elutes earlier on C18 silica) than the starting material, but more lipophilic (ie. elutes later on C18 silica) than compound VI. Once no more of compound XVI was detected by HPLC, the reaction mixture was evaporated to dryness and then purified by column chromatography as follows. Normal phase silica, in a 75:1 ratio of silica to compound, was solvated in a 1:2 mixture of EtOAc and heptane. The mobile phase was a step gradient, increasing the polarity of the solvent system by increasing the EtOAc concentration until the entire desired product is eluted. All fractions that appeared clean by HPLC (>95%) were pooled and concentrated to give pure compound XXI. Compound XXI has the structure I with $R^1$=—$CH_2$—$C_6H_5$; $R^2$=—$CH_2C_6H_5$; $R^3$=—$C_6H_4$—O—C(=O)—$CH_3$; and $R^4$=H.

Compound XXI thus has a deprotected enol/carbonyl which can be protected to provide an unsymmetrical protected luminophore. For example, reaction with bromomethyl acetate will produce protected luminophore XVIII.

Example No. 6

In this example, a protected luminophore bearing two acetyl protecting groups (on the phenol groups) and one acetoxymethyl protecting group was synthesized from the protected luminophore (IX) synthesized in Example 1. To a 1% solution of IX in anhydrous pyridine was added NaH (5.0 equivalents), and the solution was allowed to stir at room temperature under an inert atmosphere. After 10 minutes, bromomethyl acetate (5.0 eq.) was added dropwise to the mixture, and the reaction mixture was stirred at room temperature for an additional 30 minutes. To the reaction was added $CH_2Cl_2$, in an volume double that of the pyridine, followed by $H_2O$, in an volume equal to that of the pyridine. This mixture was stirred for 5 more minutes, the layers were then separated, and the organic layer was evaporated to dryness. This material can be purified by column chromatography using normal phase silica with EtOAc/heptane as the mobile phase to yield compound XVII.

Example No. 7

In this example, a protected luminophore having structure XIX was synthesized from a coelenterazine having structure VII, using a modification of the procedure of Aungst, et al (*Pharmaceutical Research*, 12(5), 763 (1995)). To a mixture of KI (0.122 g, 0.74 mM), $K_2CO_3$ (0.031 g, 0.44 mM) and chloromethyl pivalate (1.1 g, 7.3 mM) in dry DMF (3 mL) was added compound VII (0.3 g, 0.73 mM), and the reaction was stirred overnight at room temperature under an inert atmosphere. Analysis by HPLC showed complete consumption of compound VII and appearance of a less polar peak correlated to compound XIX. The DMF was evaporated under reduced pressure. The solid was dissolved in $CH_2Cl_2$ and purified by chromatography on 50 g of N.P silica to yield 255 mgs of compound XIX (98% pure by HPLC).

Example No. 8

In this example, a coelenterazine having structure VIII ("dideoxycoelenterazine") was synthesized from 2-amino-3-benzyl-5-phenylpyrazine and 2-acetoxy-3-phenylypropenal. The compound 2-amino-3-benzyl-5-phenylpyrazine was prepared according to previously described methods (Kishi, Y. et al, *Tet. Lett.* 2747 (1972); Cormier, M. et al, *Biochemistry*, 18(11), 2204 (1979); Hirano, T. et al *Tetrahedron* 53 (38) 12903-12916 (1997)). The compound 2-acetoxy-3-phenylypropenal was synthesized as follows. To a solution of phenylpyruvic acid (25 g, 152 mM) in dry pyridine (250 mL) was added acetic anhydride (170 mL). The solution was stirred overnight under an inert atmosphere and monitored by thin layer chromatography (TLC) using 10% methanol in $CH_2Cl_2$. The pyridine was evaporated under reduced pressure, and the resulting syrup was taken up in $CH_2Cl_2$ (700 mL) and washed 3 times with 200 mL portions of a 0.1N aqueous HCl solution. The organic phase was dried over $Na_2SO_4$ and filtered, and the filtrate was concentrated under reduced pressure to a viscous amber syrup. This syrup was purified by chromatography on N.P. silica with $CH_2Cl_2$ to give 24 g of 2-acetoxy-3-phenylpropenoic acid. This enol acetate intermediate was dissolved in 150 mL THF and cooled to 0° C. Oxalyl chloride (51 mL, 580 mM) was then added dropwise with stirring, and the solution allowed to stir for an additional 20 minutes at 0° C. Dimethylformamide (DMF) (7.5 mL) was added dropwise, and this solution was then stirred for 4 hours at 0° C., concentrated under reduced pressure and co-evaporated twice with toluene to yield the acid chloride. This acid chloride intermediate (14.5 g, 87 mM) was dissolved in 200 mL of a 1:1 $CH_2Cl_2$/THF mixture. This solution was cooled to −70° C., and LiAl(OtBu)$_3$H (152 mL, 152 mM) was added dropwise while maintaining the temperature of the reaction below −70° C. After addition of LiAl(OtBu)$_3$H was complete, stirring was continued for 2 hours at −70° C. The cooling bath was removed, aqueous HCl (2N, 100 mL) was added and the reaction was allowed to warm to room temperature. The mixture was extracted into 500 mL ether, and the combined organic phases were dried over $Na_2SO_4$ and filtered. The filtrate was concentrated under reduced pressure to yield a viscous oil, which was purified by column chromatography using N.P. silica (250 g) and a step gradient of ethyl acetate in hexane. The desired compound was eluted in 10% ethyl acetate in heptane to yield 13.5 g of 2-acetoxy-3-phenylpropenal as an amber oil (80% yield, aldehyde singlet at 9 ppm in $^1$H NMR, ms.=189).

Dideoxycoelenterazine was prepared from 2-amino-3-benzyl-5-phenylpyrazine and 2-acetoxy-3-phenylypropenal according to the previously described method of Kishi, et al (*Tet. Lett.,* 1972) with the following modifications. To a solution of 2-amino-3-benzyl-5-phenylpyrazine (2 g, 8.1 mM) in ethanol (125 mL) was added 2-acetoxy-3-phenylypropenal (3 g, 16.2 mM) all at once. This solution was deoxygenated for 30 minutes by passing argon gas through the solution. Concentrated aqueous HCl (4 mL) was added, and the reaction was heated at reflux for 18 hrs. After cooling to room temperature, the off-white precipitate was collected by filtration, washed with 40 mL ethanol, and dried under vacuum to yield 1.28 gms of compound VIII, dideoxycoelenterazine (80% yield).

Compound VIII thus has a deprotected enol/carbonyl which can be protected to provide a protected luminophore. For example, reaction with bromomethyl acetate will produce protected luminophore XX.

in vitro Analyses

Example No. 9

Stability of Various Protected Luminophores

Samples of a coelenterazine or a protected luminophore were dissolved in methanol at concentrations of approximately 3 mM. These stocks were diluted to 1 µM in F12 medium; F12 medium+10% Fetal Bovine Serum; or F12 medium+0.01% Tween 20. Samples were taken at different times, and the amount of the compound (coelenterazine or protected luminophore) remaining in the sample was measured using HPLC. The half-life of the compound in each solution was determined by performing regression analysis on the linear function created by plotting the logarithm of the absorbance vs. time. The time required for the concentration of the compound to fall to 50% of the initial concentration was then calculated.

TABLE C

| | Half-life (min) | | | | | | |
|---|---|---|---|---|---|---|---|
| | VI | XVII | VII | XVIII | XIX | VIII | XX |
| F12 Medium + FBS | 17 | 92 | 35 | 55 | 1155 | 40 | 92 |
| F12 + 0.01% Tween 20 | 55 | 866 | | | | | |
| F12 + FBS (37° C.) | | | 25 | | 866 | | | in situ Analyses

In these examples, the behavior of luminophores and protected luminophores were examined in situ in a variety of cultured cells. Cells were transiently or stably transfected with a plasmid encoding *Renilla* luciferase. Luminescence was compared between cells contacted with a coelenterazine (VI or VII) or a protected luminophore (IX, XV, or XVI). By measuring luminescence over time and comparing the luminescence to those in which no cells were present, it is demonstrated that contacting the cells with protected luminophore leads to generally lower luminescence, with a longer half-life, and higher signal-to-background ratio over cells contacted with unmodified coelenterazine.

Chinese hamster ovary (CHO) cells were maintained in Ham's F-12 media supplemented with 10% fetal bovine serum (FBS). HeLa and 293 cells were maintained in DMEM media supplemented with 10% fetal calf serum (FCS). All cell lines were grown at 37° C. in the presence of 5% $CO_2$. Cells were transiently transfected with either 15 µg pUC19 or pRL-Control plasmid (PROMEGA CORPORATION, E6271) at a concentration of $7.5 \times 10^5$ cells per 10 cm plate using Tfx-20 (PROMEGA CORP., E2391) or TransFast™ Transfection Reagent (PROMEGA CORP., E2431). The following day, transfections were pooled and split into 48 wells of a white DYNEX 96-well luminometer plate.

CHO cells were also independently stably transfected with pHRL-Control and pPGKNeo (plasmid expressing Neomycin gene for clonal selection) using TransFast™ reagent. Following clonal selection in 500 µg/ml Neomycin (PROMEGA CORP.), stable clones were selected for *Renilla* luciferase activity using coelenterazine in complete F12 medium.

The cells thus prepared were then subjected to a variety of assays. Reaction buffers for these assays were prepared using either DMEM or F12 media with FBS or FCS (10% by volume). Coelenterazine VI, coelenterazine VII or one of protected luminophores IX, XV, or XVI was then added to yield a concentration of 60 µM. These buffers were then used for luminescence measurements in the following assays. Luminescence was measured using an ORION luminometer.

Example No. 10

Live Cell Assay, with Increase in Signal to Background Ratio

Media was aspirated from the cells after 24 or 48 hours following transfection. The cells were washed with 100 µl per well of 1× phosphate buffered saline. Reaction buffer containing either VI or IX was titrated into complete media by half-logs, and these solutions were added to empty wells and to wells containing transfected cells. Luminescence was measured 5 minutes after media replacement. Immediately following the initial measurement, TERGITOL NP-9 (SIGMA CHEMICALS) was added to a final concentration of 1%. Samples were mixed for approximately 15 seconds, and luminescence was integrated over 1 second per well. The luminescence measured from cell samples increased after Tergitol NP-9 was added to samples containing coelenterazine VI or VII. The luminescence measured from cell samples dropped almost to the level of autoluminescence after Tergtiol NP-9 was added to samples containing coelenterazines IX, XV, or XVI or XIX.

Autoluminescence was taken as the luminescence measured for samples containing medium and serum alone. The luminescence divided by the autoluminescence was taken as the signal to background ratio (S/B). The results for CHO cells transfected with pHRL CMV, E6271 are given in Table D.

TABLE D

| Compound | Reference Compound | Ratios - compound/reference | | |
|---|---|---|---|---|
| | | Autolum. | Luminesc. | S/N |
| IX | VI | 0.2 | 1.5 | 9.1 |
| XV | VI | 0.2 | 0.7 | 3.9 |
| XVI | VI | 0.4 | 1.1 | 3.4 |
| XVI | VII | 0.9 | 1.4 | 1.7 |
| XIX | VII | 0.2 | 0.32 | 17 |

Example No. 11

Comparison of Autoluminescence

Figure 2:
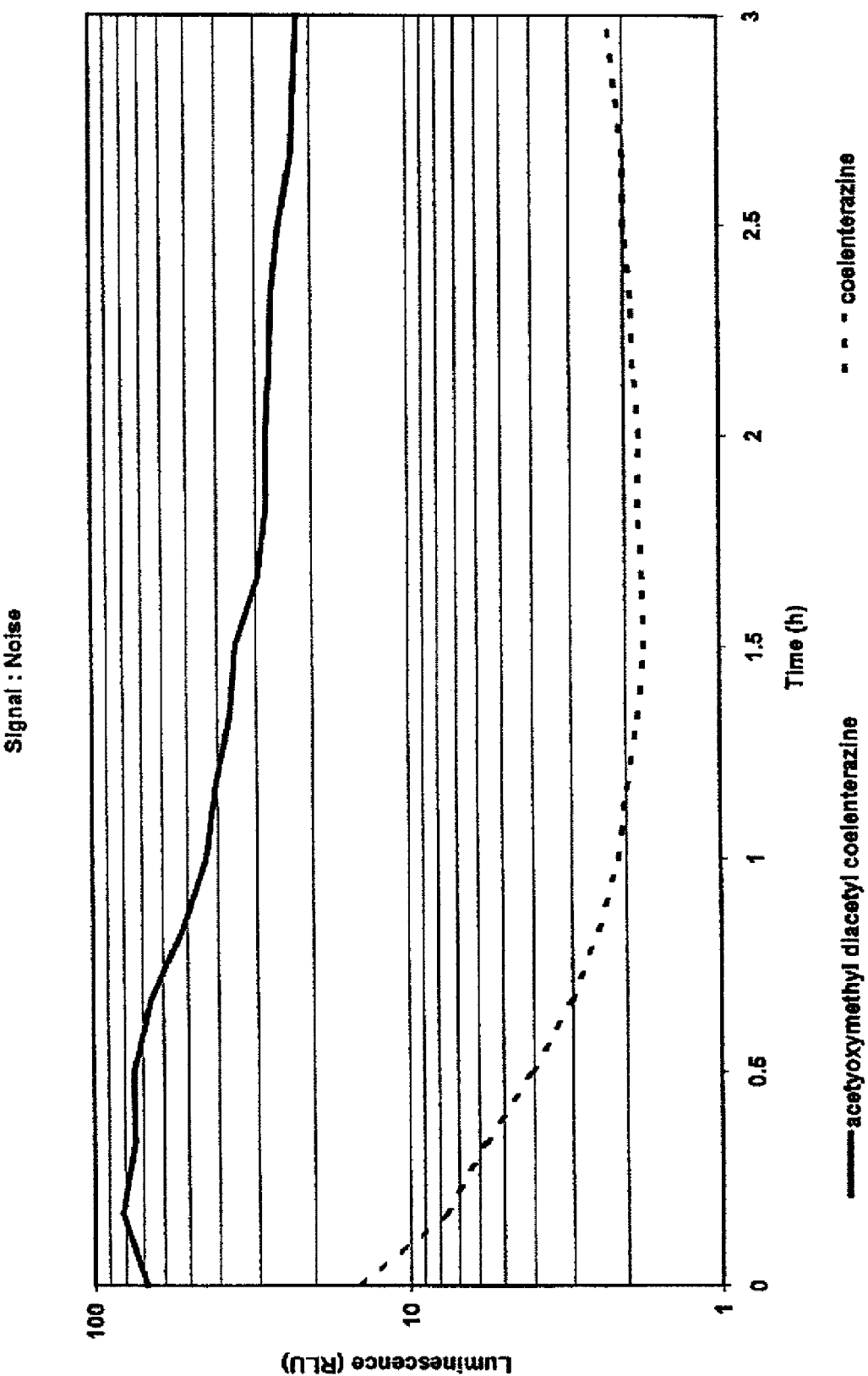
FIG. 2 is a graph of signal-to-background ratios.

CHO cells, stably transfected with synthetic the *Renilla* luciferase gene under the control of the CMV promoter (PROMEGA, inventory), were grown in F12 medium containing 10% FBS at 37° C. in the presence of 5% CO2. Cells were seeded in 3 rows of a 96-well plates (rows A-C) and left to grow overnight. Coelenterazine VI or acetoxymethyl diacetyl coelenterazine XVII were diluted to 60 µM in F12 medium+10% FBS. The F12 containing coelenterazine XVII was used to replace the medium in row A and was also added to the empty wells in row E (to permit the measurement of autoluminescence). The F12 containing coelenterazine was used to replace the medium in row C and was also added to the empty wells in row G. Row B was used to ensure that no luminescence was generated in the absence of coelenterazine or acetoxymethyl diacetyl coelenterazine. The luminescence from the wells on this plate were measured every 10 minutes for 3 hours, and graphed as the luminescence (luminogenic protein-dependent luminescence) and the autoluminescence (the lumingenic protein-independent luminescence measured from wells that did not contain cells) for each compound over time. The luminescence measured as a function of time is shown in the graph of FIG. 1. The signal-to-background ratios are shown in the graph of FIG. 2.

Example No. 12

Short Half-life Genetic Reporters

This example shows the effect of blocking two parts of a protein synthesis pathway. Puromycin and cycloheximide both inhibit protein synthesis, but they do it in different ways at different points in the pathway. In vitro, the enzyme will decrease more than 100 fold in intensity, and with a half-life of 3-5 minutes at 22° C.

Figure 3:
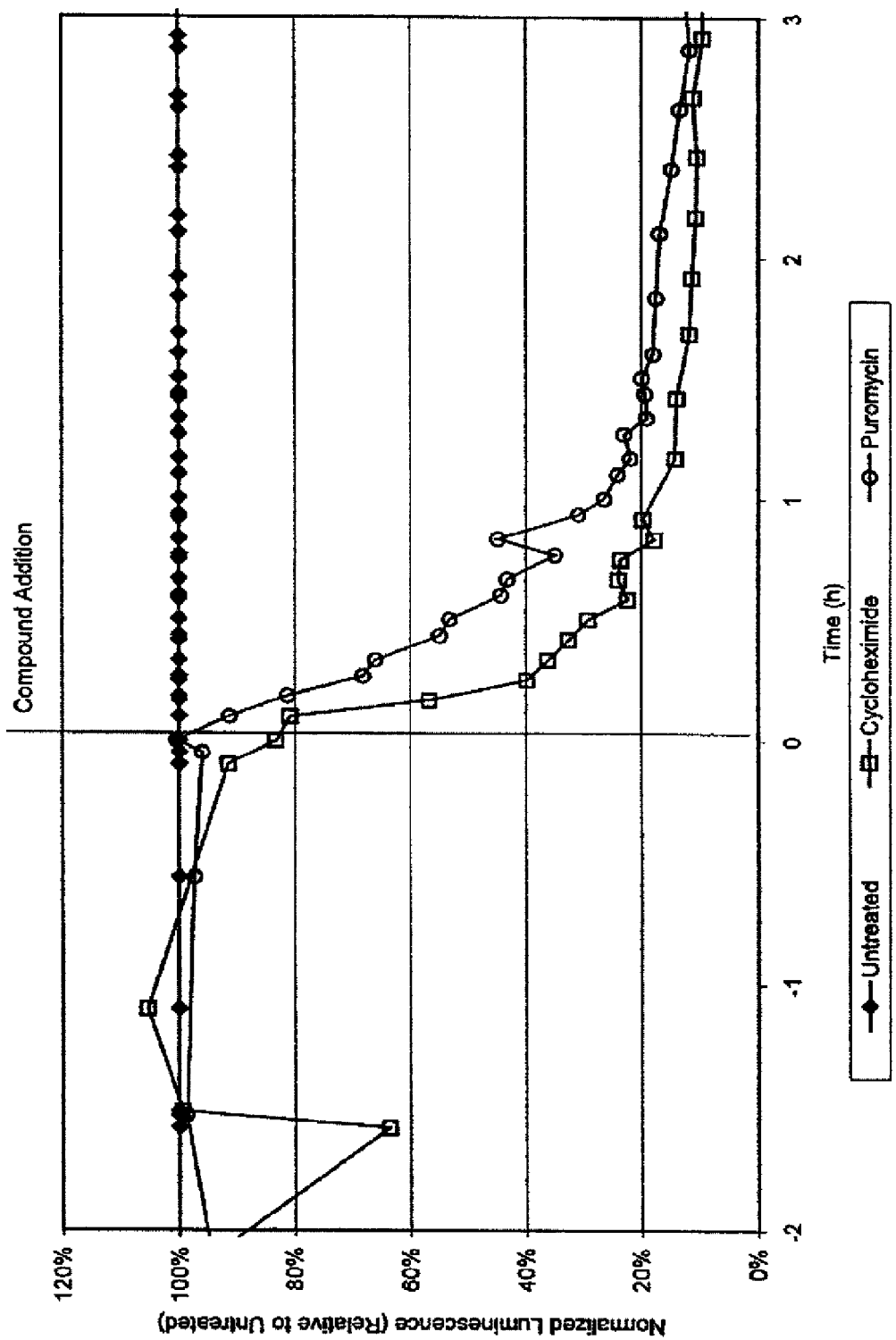
FIG. 3 is a graph of luminescence for each time normalized to the average luminescence measured for untreated samples, measured at the same time.

CHO cells were stably transfected with the synthetic humanized *Renilla* luciferase gene under the control of the CMV promoter (Promega, inventory) and grown in 96 well plates in F12 medium containing 10% Fetal bovine Serum at 37° C. in the presence of 5% CO2. A series of 12-16 plates were seeded in row A only and left overnight to grow. The medium was removed and replaced with F12 medium+10% FBS containing 600 μM POM coelenterazine-h (XIX). The luminescence from the cells on one plate was measured, and all plates were returned to the incubator. The luminescence from the cells on one plate was measured each hour for 1, 2, and 3 hours post-medium replacement. The luminescence was also measured at approximately 3.5 hours post-medium replacement. Puromycin or cycloheximide was added to half of the wells on each plate, and the plates were returned to the incubator. This was considered time 0. At time 0, the luminescence from the cells on one plate was measured. At 5 minute intervals, the plate was returned to the incubator and a new plate was removed and the luminescence measured. This cycle was repeated every 5 minutes until the rate of change decreased. At this time, a single plate would be removed and its luminescence would be measured. The plate would then be promptly returned to the incubator. This cycle would be repeated at approximately 15 minute intervals. The luminescence measured in all of these plates was averaged as "untreated cells" (those not exposed to protein inhibitor) and "treated cells" (those exposed to cycloheximide or puromycin). The data is shown graphically in FIG. 3 as luminescence for each time normalized to the average luminescence measured for the untreated samples, measured at the same time. The absolute luminescence for the untreated samples remained consistent from time 0 until the end of the analysis.

Example No. 13

Assay for Localization of Luminescence from Coelenterazine Derivative Versus Coelenterazine Parent Compound A. POM-h (XIX) v. Coelenterazine-h (VII)

CHO hRL25 cells (which express luciferase) (4.5 mL of $(7.5 \times 10^5$ cells)/(plate/$5 \times 10^9$ cells/mL) were resuspended in 5.5 mL media and put into 96 well plates. The next day, the cells were aspirated, washed with 100 μL PBS, and then aspirated again. 100 μL of media (F12) containing no substrate (background) was then added to wells containing no cells. These wells were then read for 1 sec/well with an ORION Luminometer (BERTHHOLD) (Table E; Bkg).

Similarly, 100 μL portions of media containing 100 μM of either POM-h or coelenterazine-h were placed in wells containing cells or wells alone. These wells were then read for 1 sec/well with an ORION Luminometer (BERTHHOLD) immediately following (coelenterazine) and 10 minutes post-addition (POM-h) (Table E; Subs).

Thereafter, 0.5 μL of purified *Renilla* luciferase ($3.96 \times 10^{-5}$ M/Reaction (Chemicon) was added to each well. All wells were then read for 1 second/well (Table E; RL).

TABLE E

|  | Bkg | Subs (RLU) | RL (RLU) |
|---|---|---|---|
| hRL25 + coelenterazine-h (VII) | 18 | 39342 | 331381 |
| hRL25 + POM-h (XIX) | 23 | 19584 | 35349 |
| Media + coelenterazine-h (VII) | 19 | 763 | 278467 |
| Media + POM-h (XIX) | 16 | 21 | 3641 |

The above data using CHO hRL25 cells, which express luciferase, demonstrate that POM-h is converted into a luminophore both before and after exogenous addition of luciferase to the media (19584 v. 35349), suggesting that this substrate is quickly localized within cells. In contrast, under similar conditions, coelenterazine-h has a lower luminescence pre addition of exogenous luciferase compared to post addition (39342 v. 331381), suggesting that this substrate can be used inside as well as outside the cell, without the need for a complex containing an esterase.

These data further demonstrate that, in media only (with little esterase), POM-h has low luminescence compared to hRL25 cell-containing media (3641 v. 35349), demonstrating that this coelenterazine derivative must first be converted by an esterase before it can be converted into a luminophore by luciferase. In contrast, coelenterazine-h exhibits comparable luminescence both with media only and with hRL25 cell-containing media (278467 v. 331381), suggesting that no cell mediated conversion is necessary before it can react with exogenous luciferase.

B. Triacetyl Coelenterazine (IX) v. Coelenterazine (VI)

Untransfected CHO (which do not naturally produce luciferase) and CHO hRL25 cells (which express luciferase) (4.5 mL of $(7.5 \times 10^5$ cells)/(plate/$5 \times 10^9$ cells/mL) were resuspended in 5.5 mL media and put into 96 well plates. The next day, the cells were aspirated, washed with 100 μL PBS, and then aspirated again. 100 μL of media (F12) containing no substrate (background) was then added to wells containing no cells. These wells were then read for 1 sec/well with an ORION Luminometer (BERTHHOLD) (Table F; Bkg).

Similarly, 100 μL portions of media (F12) containing 100 μM of either coelenterazine or triacetyl coelenterazine were placed in wells containing cells or wells alone. These wells were then read for 1 sec/well with an ORION Luminometer (BERTHHOLD) immediately following (coelenterazine) and 4 minutes post-addition (triacetyl coelenterazine) (Table F; Subs).

Thereafter, 0.5 μL of purified *Renilla* luciferase ($3.96 \times 10^{-5}$ M/Reaction (Chemicon) was added to each well. All wells were then read for 1 second/well (Table F; RL).

TABLE F

| | Bkg | Subs (RLU) | RL (RLU) |
|---|---|---|---|
| hRL2 + triacetyl coelenterazine (IX) | 23 | 224353 | 229111 |
| hRL2 + coelenterazine (VI) | 23 | 139842 | 110008374 |
| CHO + triacetyl coelenterazine (IX) | 23 | 864 | 8910 |
| CHO + coelenterazine (VI) | 23 | 6253 | 11930147 |

The invention claimed is:

1. A method of measuring luminogenic activity of a luminogenic protein comprising:
    contacting a luminogenic protein, a deprotecting enzyme, and a protected luminophore in solution to form a composition; and
    detecting light produced from the composition;
    wherein the protected luminophore includes an imidazolone oxygen protected with a protecting group, and the protecting group together with the imidazolone oxygen to which it is attached is an ester, an acetyl, a butyryl, an acetoxymethyl, a propanoyloxymethyl, a butyryloxymethyl, a pivaloyloxymethyl group or —C(=O)—C(CH$_3$)$_3$;
    wherein the deprotecting enzyme is capable of removing the protecting group from the protected luminophore.

2. The method of claim 1, wherein the luminogenic protein is *Renilla* luciferase.

3. The method of claim 1, wherein the protected luminophore is a compound of formula (XII)

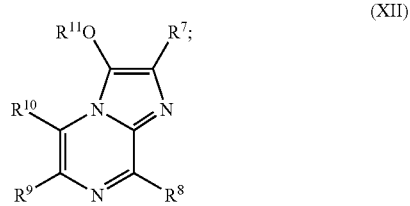

wherein R$^7$ is H, alkyl, heteroalkyl, aryl, or —CH$_2$—C$_6$H$_4$OR$^{14}$;
R$^8$ is H, alkyl, heteroalkyl, or aryl;
R$^9$ is H, alkyl, heteroalkyl, aryl, or —C$_6$H$_4$OR$^{15}$;
R$^{10}$ is —H, —CH$_3$, or —CH(CH$_3$)$_2$;
R$^{14}$ and R$^{15}$ are each independently a protecting group; and
R$^{11}$ together with the oxygen atom to which it is attached is an ester, an acetyl, a butyryl, an acetoxymethyl, a propanoyloxymethyl, a butyryloxymethyl, a pivaloyloxymethyl group or —C(=O)—C(CH$_3$)$_3$.

4. The method of claim 3, wherein
R$^7$ is —CH$_2$—C$_6$H$_5$, naphthyl, —CH$_2$—C$_6$H$_4$OH, —CH$_2$—C$_6$H$_4$F, or —CH$_2$—C$_6$H$_4$OR$^{14}$;
R$^8$ is —CH$_2$C$_6$H$_5$, —CH$_2$C$_6$H$_{11}$, —CH$_2$C$_5$H$_9$, or —(CH$_2$)$_3$NHC(=NH)NH$_2$; and
R$^9$ is phenyl, indolyl, —C$_6$H$_4$OH, —C$_6$H$_4$NH$_2$, —C$_6$H$_4$F, or —C$_6$H$_4$OR$^{15}$.

5. The method of claim 3, wherein —OR$^{11}$, —OR$^{14}$, and —OR$^{15}$ are each independently esters.

6. The method of claim 3, wherein R$^{11}$, R$^{14}$, and R$^{15}$ are independently acetyl, butyryl, acetoxymethyl, propanoyloxymethyl, butyryloxymethyl, or pivaloyloxymethyl.

7. The method of claim 6 wherein the protected luminophore is a compound of formula:

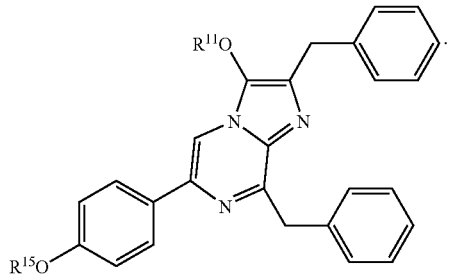

8. The method of claim 3, wherein the protected luminophore is a compound of formula:

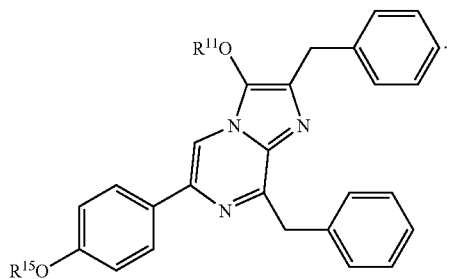

9. The method of claim 1, wherein the protected luminophore is a compound of formula (XIII) or (XIV)

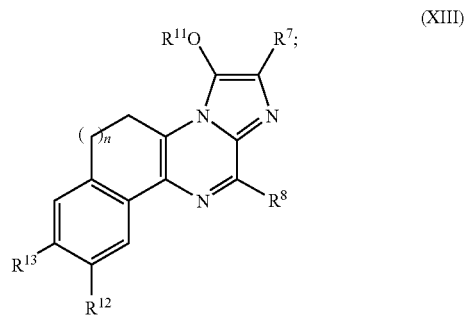

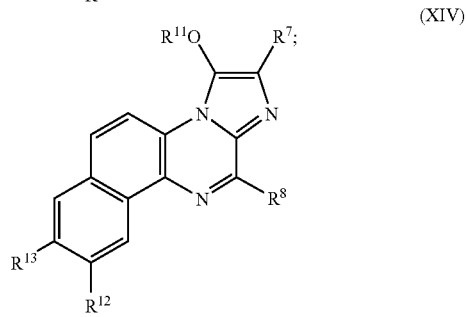

wherein R$^7$ is H, alkyl, heteroalkyl, aryl, or —CH$_2$—C$_6$H$_4$OR$^{14}$;
R$^8$ is H, alkyl, heteroalkyl, or aryl;
R$^{12}$ and R$^{13}$ are independently —H, —OH, alkyl, heteroalkyl, aryl, or —OR$^{16}$;
n is 0, 1, or 2;
R$^{14}$ and R$^{16}$ are each independently a protecting group; and R[11] together with the oxygen atom to which it is attached is an ester, an acetyl, a butyryl, an acetoxymethyl, a propanoyloxymethyl, a butyryloxymethyl, a pivaloyloxymethyl group or —C(=O)—C(CH$_3$)$_3$.

10. The method of claim 9, wherein
R[7] is —CH$_2$—C$_6$H$_5$, naphthyl, —CH$_2$—C$_6$H$_4$OH, —CH$_2$—C$_6$H$_4$F, or —CH$_2$—C$_6$H$_4$OR[14]; and
R[8] is —CH$_2$C$_6$H$_5$, —CH$_2$C$_6$H$_{11}$, —CH$_2$C$_5$H$_9$, or —(CH$_2$)$_3$NHC(=NH)NH$_2$.

11. The method of claim 9, wherein —OR[11], —OR[14], and —OR[16] are each independently esters.

12. The method of claim 9, wherein R[11], R[14], and R[16] are independently acetyl, butyryl, acetoxymethyl, propanoyloxymethyl, butyryloxymethyl, or pivaloyloxymethyl.

13. The method of claim 9, wherein n is 1.

14. The method of claim 1, wherein the composition comprises a cell.

15. The method of claim 1, wherein the composition comprises a cell which contains the deprotecting enzyme.

16. The method of claim 15, wherein detecting light produced from the composition indicates the location of the deprotecting enzyme in a cell.

17. The method of claim 1, wherein the composition comprises a cell lysate.

18. The method of claim 1, wherein the deprotecting enzyme is an esterase.

19. The method of claim 1, wherein the solution is an aqueous solution.

20. The method of claim 1, wherein the solution comprises DMSO.

21. The method of claim 1, wherein the protected luminophore is a modified coelenterazine;
wherein the enol group has been converted to an ester or an ether comprising an enzyme-removable group.

22. A method of generating luminescence in a living cell comprising a luciferase, the method comprising:
contacting the cell in solution with a protected luminophore;
wherein the protected luminophore includes an imidazolone oxygen protected with a protecting group, and the protecting group together with the imidazolone oxygen to which it is attached is an ester, an acetyl, a butyryl, an acetoxymethyl, a propanoyloxymethyl, a butyryloxymethyl, a pivaloyloxymethyl group or —C(=O)—C(CH$_3$)$_3$.

23. The method of claim 22, wherein the protected luminophore is a modified coelenterazine;
wherein the enol group has been converted to an ester or an ether comprising an enzyme-removable group.

24. The method of claim 22, wherein the protected luminophore is a compound of formula (XII)

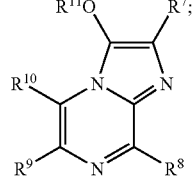

(XII)

wherein R[7] is H, alkyl, heteroalkyl, aryl, or —CH$_2$—C$_6$H$_4$OR[14];

R[8] is H, alkyl, heteroalkyl, or aryl;

R[9] is H, alkyl, heteroalkyl, aryl, or —C$_6$H$_4$OR[15];

R[10] is —H, —CH$_3$, or —CH(CH$_3$)$_2$; and

R[14] and R[15] are each independently a protecting group; and

R[11] together with the oxygen atom to which it is attached is an ester, an acetyl, a butyryl, an acetoxymethyl, a propanoyloxymethyl, a butyryloxymethyl, a pivaloyloxymethyl group or —C(=O)—C(CH$_3$)$_3$.

25. The method of claim 22, wherein the protected luminophore is a compound of formula (XIII) or (XIV)

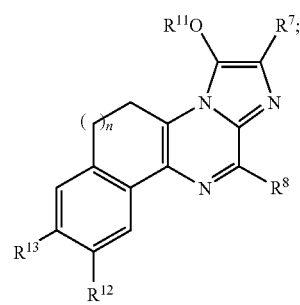

(XIII)

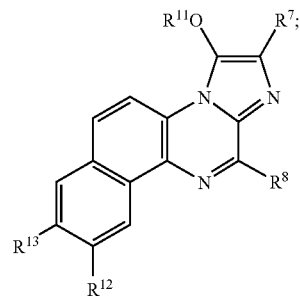

(XIV)

wherein R[7] is H, alkyl, heteroalkyl, aryl, or —CH$_2$—C$_6$H$_4$OR[14];

R[8] is H, alkyl, heteroalkyl, or aryl;

R[12] and R[13] are each independently —H, —OH, alkyl, heteroalkyl, aryl, or —OR[16];

n is 0, 1, or 2;

R[14] and R[16] are each independently a protecting group; and

R[11] together with the oxygen atom to which it is attached is an ester, an acetyl, a butyryl, an acetoxymethyl, a propanoyloxymethyl, a butyryloxymethyl, a pivaloyloxymethyl group or —C(=O)—C(CH$_3$)$_3$.

* * * * *